(12) United States Patent
Lonky

(10) Patent No.: US 10,201,332 B1
(45) Date of Patent: Feb. 12, 2019

(54) DEVICE AND METHOD OF ORIENTING A BIOPSY DEVICE ON EPITHELIAL TISSUE

(71) Applicant: Neal M. Lonky, Yorva Linda, CA (US)

(72) Inventor: Neal M. Lonky, Yorva Linda, CA (US)

(73) Assignee: HEALOE LLC, Yorba Linda, CA (US)

( * ) Notice: Subject to any disclaimer, the term of this patent is extended or adjusted under 35 U.S.C. 154(b) by 331 days.

(21) Appl. No.: 13/830,761

(22) Filed: Mar. 14, 2013

Related U.S. Application Data

(60) Provisional application No. 61/732,800, filed on Dec. 3, 2012.

(51) Int. Cl.
*A61B 10/02* (2006.01)

(52) U.S. Cl.
CPC .................. *A61B 10/02* (2013.01)

(58) Field of Classification Search
CPC .................. A61B 10/0291; A61B 2010/0216
See application file for complete search history.

(56) References Cited

U.S. PATENT DOCUMENTS

| | | | |
|---|---|---|---|
| 1,795,500 | A | 3/1931 | Omundson |
| 2,675,572 | A | 4/1954 | Nomiya |
| 2,701,559 | A | 2/1955 | Cooper |
| 2,717,437 | A | 9/1955 | De Mestral |
| 2,839,049 | A | 6/1958 | Maclean |
| 2,847,005 | A | 8/1958 | Bourne |
| 2,955,591 | A | 10/1960 | Maclean |
| 3,018,498 | A | 1/1962 | Wasserman |
| 3,263,681 | A | 8/1966 | Nechtow |
| 3,511,242 | A | 5/1970 | Agnone |
| 3,554,185 | A | 1/1971 | Kohl |
| 3,559,226 | A | 2/1971 | Burns |
| 3,628,522 | A | 12/1971 | Kato |
| 3,774,590 | A | 11/1973 | McDonald |
| 3,777,743 | A | 12/1973 | Binard et al. |
| RE27,915 | E | 2/1974 | Kohl |
| 3,796,211 | A | 3/1974 | Kohl |

(Continued)

FOREIGN PATENT DOCUMENTS

| | | |
|---|---|---|
| AT | 392411 | 7/1988 |
| CH | 653880 | 1/1986 |

(Continued)

OTHER PUBLICATIONS

Australian Patent Exam Report 20130806, dated Aug. 6, 2013, 5 pages.

(Continued)

*Primary Examiner* — Rene Towa
*Assistant Examiner* — H. Q. Nguyen
(74) *Attorney, Agent, or Firm* — SCI-Law Strategies, PC

(57) ABSTRACT

In various embodiments of the invention, a tissue biopsy sampling device is located or oriented on a site within a body cavity or canal with a retention device. In various embodiments of the invention, a tissue biopsy sampling device is retained or held in place on a desired specific location on the epithelial tissue with the retention device. In various embodiments of the invention, the epithelial tissue within the cavity or canal is presented to the tissue biopsy sampling device using the retention device. In various embodiments of the invention, the retention device is used to assist withdrawal of the tissue biopsy sampling from within the body cavity or canal.

20 Claims, 12 Drawing Sheets

(56) References Cited

U.S. PATENT DOCUMENTS

| | | |
|---|---|---|
| 3,877,464 A | 4/1975 | Vermes |
| 3,945,372 A | 3/1976 | Milan et al. |
| 4,016,865 A | 4/1977 | Fredericks |
| 4,061,146 A | 12/1977 | Baehr et al. |
| 4,127,113 A | 11/1978 | Nollan |
| 4,168,698 A | 9/1979 | Ostergard |
| 4,227,537 A | 10/1980 | Suciu et al. |
| 4,245,653 A | 1/1981 | Weaver |
| 4,384,587 A | 5/1983 | Milgrom |
| 4,396,022 A | 8/1983 | Marx |
| 4,430,076 A | 2/1984 | Harris |
| 4,465,072 A | 8/1984 | Taheri |
| 4,467,816 A | 8/1984 | Schluter |
| 4,620,548 A | 11/1986 | Hasselbrack |
| 4,641,662 A | 2/1987 | Jaicks |
| D289,926 S | 5/1987 | Lonky |
| 4,700,713 A | 10/1987 | Kist |
| 4,754,764 A | 7/1988 | Bayne |
| 4,757,826 A | 7/1988 | Abdulhay |
| 4,759,376 A | 7/1988 | Stormby |
| 4,762,133 A | 8/1988 | Bayne et al. |
| 4,763,669 A | 8/1988 | Jaeger |
| 4,777,947 A | 10/1988 | Zwick |
| 4,781,202 A | 11/1988 | Janese |
| 4,872,243 A | 10/1989 | Fischer |
| 4,873,992 A | 10/1989 | Bayne |
| 4,892,831 A | 1/1990 | Wong |
| 4,932,857 A | 6/1990 | Nishino et al. |
| 4,946,389 A | 8/1990 | Weissenberger |
| 4,951,684 A | 8/1990 | McMillan |
| 4,961,430 A | 10/1990 | Sheahon |
| 4,965,725 A | 10/1990 | Rutenberg |
| 5,022,408 A | 6/1991 | Mohajer |
| 5,067,195 A | 11/1991 | Sussman |
| 5,069,224 A | 12/1991 | Zinnanti, Jr. |
| 5,092,345 A | 3/1992 | Sakita |
| 5,133,361 A | 7/1992 | Cox et al. |
| 5,154,694 A | 10/1992 | Kelman |
| 5,184,626 A | 2/1993 | Hicken |
| 5,191,899 A | 3/1993 | Strickland et al. |
| 5,197,949 A | 3/1993 | Angsupanich |
| 5,250,061 A | 10/1993 | Michelson |
| 5,253,652 A | 10/1993 | Fast |
| 5,257,182 A | 10/1993 | Luck et al. |
| 5,259,391 A | 11/1993 | Altshuler |
| 5,287,272 A | 2/1994 | Rutenberg et al. |
| 5,315,740 A | 5/1994 | Provost |
| 5,329,938 A | 7/1994 | Lonky |
| 5,370,128 A | 12/1994 | Wainwright |
| 5,421,346 A | 6/1995 | Sanyal |
| 5,445,164 A | 8/1995 | Worthen et al. |
| 5,456,265 A | 10/1995 | Yim |
| 5,462,063 A | 10/1995 | Kist et al. |
| 5,464,409 A | 11/1995 | Mohajer |
| 5,470,308 A | 11/1995 | Edwards et al. |
| 5,476,104 A | 12/1995 | Sheahon |
| 5,535,756 A | 7/1996 | Parasher |
| 5,544,650 A | 8/1996 | Boon et al. |
| 5,549,563 A | 8/1996 | Kroner |
| 5,623,941 A | 4/1997 | Hedberg et al. |
| 5,643,307 A | 7/1997 | Turkel et al. |
| 5,649,943 A | 7/1997 | Amoils |
| 5,713,369 A | 2/1998 | Tao et al. |
| 5,722,423 A | 3/1998 | Lind et al. |
| 5,738,109 A | 4/1998 | Parasher |
| 5,761,760 A | 6/1998 | Dumler et al. |
| 5,785,785 A | 7/1998 | Chesley |
| 5,792,160 A | 8/1998 | Weiss et al. |
| 5,800,362 A | 9/1998 | Kobren et al. |
| 5,807,282 A | 9/1998 | Fowler |
| 5,857,982 A | 1/1999 | Milliman et al. |
| 5,865,765 A | 2/1999 | Mohajer |
| 5,868,668 A | 2/1999 | Weiss |
| 5,899,850 A | 5/1999 | Ouchi |
| 5,913,857 A | 6/1999 | Ritchart et al. |
| 5,916,228 A | 6/1999 | Ripich |
| 5,937,870 A | 8/1999 | Gueret |
| 5,951,550 A | 9/1999 | Shirley et al. |
| 6,053,877 A | 4/2000 | Banik et al. |
| 6,101,408 A * | 8/2000 | Craine ............... A61B 1/0638 128/922 |
| 6,132,421 A | 10/2000 | Clapham |
| 6,193,674 B1 | 2/2001 | Zwart |
| 6,258,044 B1 | 7/2001 | Lonky et al. |
| 6,297,044 B1 | 10/2001 | Eisen et al. |
| 6,336,905 B1 | 1/2002 | Colaianni |
| 6,346,086 B1 | 2/2002 | Maksem et al. |
| 6,376,905 B2 | 4/2002 | Hisano et al. |
| 6,379,315 B1 | 4/2002 | Claren |
| 6,387,058 B1 | 5/2002 | Wallach |
| 6,394,966 B1 | 5/2002 | Gill et al. |
| 6,494,845 B2 | 12/2002 | Rutenberg |
| 6,595,947 B1 | 7/2003 | Mikszta |
| 6,676,609 B1 | 1/2004 | Rutenberg et al. |
| 6,730,085 B2 | 5/2004 | George et al. |
| 6,740,049 B2 | 5/2004 | Wallach |
| 6,790,654 B2 | 9/2004 | Malinge |
| 6,860,738 B2 | 3/2005 | Bachmann |
| 6,918,880 B2 * | 7/2005 | Brookner ............... A61B 10/02 600/565 |
| 7,004,913 B1 | 2/2006 | Rutenberg et al. |
| 7,137,956 B2 | 11/2006 | Nishtalas et al. |
| 7,156,814 B1 | 1/2007 | Williamson, IV et al. |
| 7,157,233 B2 | 1/2007 | Fischer et al. |
| 7,413,551 B2 | 8/2008 | Decker et al. |
| D605,407 S | 12/2009 | Wagner |
| 7,749,173 B2 | 7/2010 | Larkin |
| 7,836,539 B2 | 11/2010 | Moskovich |
| 7,871,574 B2 | 1/2011 | Peltier |
| 8,152,739 B1 | 4/2012 | McCully |
| 8,348,856 B1 | 1/2013 | Malanowska |
| 8,439,847 B2 | 5/2013 | Larkin |
| 8,517,956 B1 | 8/2013 | Malanowska |
| 8,617,183 B2 | 12/2013 | Schneider |
| 8,652,067 B2 | 2/2014 | Lonky |
| 8,795,197 B2 | 8/2014 | Lonky |
| 9,044,213 B1 | 6/2015 | Lonky |
| 9,282,950 B2 | 3/2016 | Klein |
| 9,282,951 B2 | 3/2016 | Lonky |
| 9,393,394 B2 | 7/2016 | Lonky |
| 9,687,642 B2 | 6/2017 | Lonky |
| 9,895,140 B1 | 2/2018 | Lonky |
| 2001/0022063 A1 | 9/2001 | Korteweg et al. |
| 2002/0068881 A1 | 6/2002 | Kobren et al. |
| 2003/0109804 A1 | 6/2003 | Auerbach |
| 2004/0029658 A1 | 2/2004 | Howe |
| 2004/0120989 A1 | 4/2004 | Vadas |
| 2004/0116827 A1 | 6/2004 | Tiberio |
| 2004/0138642 A1 | 7/2004 | Fischer |
| 2004/0181170 A1 | 9/2004 | Wallach |
| 2004/0181185 A1 | 9/2004 | Lee |
| 2004/0220478 A1 | 11/2004 | Wallace et al. |
| 2004/0236247 A1 | 11/2004 | Rizvi |
| 2004/0260199 A1 | 12/2004 | Hardia |
| 2004/0260201 A1 | 12/2004 | Mueller, Jr. |
| 2004/0267191 A1 | 12/2004 | Gifford, III et al. |
| 2005/0059905 A1 | 3/2005 | Boock et al. |
| 2005/0215920 A1 | 9/2005 | Isa |
| 2005/0251093 A1 | 11/2005 | Abou-Kansoul |
| 2006/0052805 A1 | 3/2006 | Cwik |
| 2006/0200043 A1 | 9/2006 | Jannetty et al. |
| 2007/0093727 A1 | 4/2007 | Feuer et al. |
| 2007/0100335 A1 | 5/2007 | Fischer |
| 2007/0107155 A1 | 5/2007 | Kacher |
| 2007/0118947 A1 | 5/2007 | Lorenzo |
| 2007/0161042 A1 | 7/2007 | Zuk |
| 2007/0282223 A1 | 12/2007 | Larkin |
| 2008/0188769 A1 | 8/2008 | Lu |
| 2009/0012424 A1 | 1/2009 | Huschmand Nia et al. |
| 2009/0112239 A1 | 4/2009 | To |
| 2009/0149860 A1 | 6/2009 | Scribner |
| 2009/0326414 A1 | 12/2009 | Peltier |
| 2010/0210968 A1 | 8/2010 | Lonky |
| 2010/0249649 A1 | 9/2010 | Larkin |

(56) References Cited

U.S. PATENT DOCUMENTS

| | | |
|---|---|---|
| 2011/0172557 A1 | 7/2011 | Lonky |
| 2011/0268610 A1 | 11/2011 | Recknor |
| 2013/0267870 A1 | 10/2013 | Lonky |
| 2014/0128773 A1 | 5/2014 | Lonky |
| 2014/0358158 A1 | 12/2014 | Einarsson |
| 2016/0100862 A1 | 4/2016 | Parys |
| 2017/0021151 A1 | 1/2017 | Lonky |
| 2017/0112477 A1 | 4/2017 | Benning |
| 2018/0035983 A1 | 2/2018 | Lonky |

FOREIGN PATENT DOCUMENTS

| | | |
|---|---|---|
| EP | 2166965 | 7/2008 |
| WO | WO 2005/084555 | 9/2005 |
| WO | WO2007101994 | 9/2007 |
| WO | WO 2009/012392 | 1/2009 |
| WO | WO2012125757 | 9/2012 |
| WO | WO2015134568 | 9/2015 |

OTHER PUBLICATIONS

European Office Action, 08796246.0 1654, dated Jun. 5, 2015, 5 pages.

Blute, Renal brush biopsy: Survey of indications, techniques and results, J Urol., Aug. 1981, vol. 126(2), pp. 146-149.

Boon et al., "Confocal Sectioning of Thick, Otherwise Undiagnosable Cell Groupings in Cervical Smears" Acta Cytol., vol. 37, pp. 40-48 (1991).

Boon et al., "Exploiting the "Toothpick Effect" of the Cytobrush by Plastic Embedding of Cervical Samples" Acta Cytol., vol. 35, pp. 57-63 (1991).

Boon, "A model for quantitative follow-up studies of cervical lesions," Diagn Cytopathol., 1992, vol. 8(1), pp. 8-17.

Butler, B., "Kuper brush in the diagnosis of endometrial lesions," The Lancet, Dec. 1971, vol. 298(7739), pp. 1390-1392.

DeGirolami, "Histo-brush technic for endometerial tissue study," Obstet Gynecol., Dec. 1961, vol. 28(6), pp. 861-866.

Dowlatshahi et al., "Evaluation of brush cytology as an independent technique for detection of esophageal carcinoma" J Thoracic and Cardiovascular Surgery, vol. 89, No. 6, pp. 848-851, Jun. 1985.

Fennessy, "Transbronchial biopsy of peripheral lung lesions," Radiology, May 1967, vol. 88(5), pp. 878-882.

Firestone, "Needle lung biopsy, bronchial brushing and mediastinoscopy in Management of Chest Diseases," Calif Med., Sep. 1973, vol. 119(3), pp. 1-5.

Gahres et al., "Histo-brush technic for Endometrial Tissue Study", Obstet Gynecol vol. 28, pp. 861-866 (1966)—Front Page Only.

Goldstein, "Esophageal biopsy utilizing a flexible brush," Gastrointest Endosc., Aug. 1968, vol. 15(1), pp. 53-55.

Granqvist, "Colonoscopic biopsies and cytological exam in chronic ulcerative colitis," J Gastroenterology, Apr. 1980, vol. 15(3), pp. 283-288.

Hardwick, "Brush biopsy in the diagnosia of neoplasia in Bartlett's esophagus," Disease Esophagus, Oct. 1997, vol. 10(4), pp. 233-237.

Iaccarino, "Percutaneous intralesional brushing of cystic lesions of bone: a technical improvement of diagnostic cytology," Skeletal Radiol, 1990, vol. 19(3), pp. 187-190.

International Search Report of PCT/US2008/70341 published as WO2009012392 dated Oct. 22, 2008.

Johnsson, "Cytological brush techniques in malignant disease of the endometrium," Acta Obstet Gynecol Scand, Jan. 1968, vol. 47, issue 1, pp. 38-51.

Johnsson, "Cytological diagnosis of endometrial disorders with a brush technique," Acta Obstet Gynecol Scand., 1971, vol. 50(2), pp. 141-148.

Kovnat, "Bronchial brushing through the flexible fiberoptic bronchoscope in the diagnosis of peripheral pulmonary lesions," Chest, Feb. 1975, vol. 67(2), pp. 179-184.

Liu, "Transcervical chorionic villus biopsy with a brush," Prenat Diagn., Sep.-Oct. 1985, vol. 5(5), pp. 349-355.

Maksem, "Endometrial brush cytology of advanced postmenopausal endometrium . . . ," Diagn Cytopathol., Nov. 1998, vol. 19(5), pp. 338-343.

Matsuda, "Bronchial brushing and bronchial biopsy: comparison of diagnostic accuracy and cell typing reliability in lung cancer," Thorax, Jun. 1986, vol. 41(6), pp. 475-479.

Meulman, "Predictions of various grades of cervical neoplasia on plastic-embedded cytobrush samples," Anal Quant Cytol Histol., Feb. 1992, vol. 14(1), pp. 60-72.

Mills, "Transcatheter brush biopsy of intravenous tumor thrombi," Radiology, Jun. 1978, vol. 127(3), pp. 667-670.

Morteza, "Brush and forceps biopsy of billary ducts via percutaneous transhepatic catheterization," Radiology, Jun. 1980, vol. 135, pp. 777-778.

Moskowitz, "To brush or not to brush is there really a question?," Chest, Jun. 1971, vol. 59(6), pp. 648-650.

Mullins, "A new technique for transbronchial biopsy in infants and small children," Pediatr Pulmonol, Oct. 1995, vol. 20(4), pp. 253-257.

Payne, "Diagnostic accuracy of cytology and biopsy in primary bronchial carcinoma," Thorax, Jun. 1979, vol. 43(3), pp. 294-299.

Pipkorn, "A brush to harvest cells from the nasal mucosa for microscopic and biochemical analysis," J Immunol Methods, Aug. 9, 1988, vol. 112(1), pp. 37-42.

Portner, "New devices for biliary drainage and biopsy," Radiology, Jun. 1982, vol. 138, pp. 1191-1195.

Raney, "Detection of carcinoma of upper urinary tract with steerable brush biopsy," Urology, Jul. 1979, vol. 14(1), pp. 77-78.

Ravinsky, "Cytologic features of primary adenoid cystic carcinoma of the uterine cervix. A case report," Acta Cytol., Nov.-Dec. 1996, vol. 40(6), pp. 1304-1308.

Riise et al., "Bronchial brush biopsies for studies of epithelial inflammation in stable asthma and nonobstructive chronic bronchitis" Eur Respir J vol. 9, pp. 1665-1671 (1996).

Riise, "A bronchoscopic brush biopsy study of large airway mucosal pathology in smokers . . . ," Eur Respir J., Apr. 1992, vol. 5(4), pp. 382-386.

Roth et al., "Cytologic Detection of Esophageal Squamous Cell . . . " Cancer, vol. 80, No. 11, Dec. 1, 1997.

Sanderson, "Use of a new controllable-tip brush with the flexible fiber bronchoscope," Chest, Jun. 1974, vol. 65(6), pp. 620-621.

Sheline, "Fluoroscopically guided retrograde brush biopsy in the diagnosis of transitional cell carcinoma of the upper urinary tract . . . ," Am J Roentgenology, Sep. 1989, vol. 153(2), pp. 313-316.

Willson, "Bronchial brush biopsy with a controllable brush," Am J Roentgenology, Jul. 1970, vol. 109(3), pp. 471-477.

Zavala, "Use of Bronchofiberscope for bronchial brush biopsy: diagnostic results and comparison with other brushing techniques," Chest, Jun. 1973, vol. 63(6), pp. 889-892.

Zeppa, "A model for quantitative follow-up studies of cervical lesions," Diagn Cytopathol, 1992, vol. 8(1), pp. 8-17.

Extended European Search Report, PCT/US2008/070341, dated May 11, 2012, 7 pages.

Article 94(3) European Communication, Application No. 08796246.0 PCT/US2008/070341, dated Jul. 4, 2016, 4 pages.

International Search Report, PCT/US2017/014190, dated Apr. 10, 2016, 13 pages.

ISR of Application No. 08796246, PCT/US2008/70341 published as WO2009012392 dated Oct. 22, 2008, 6 pages.

Extended ESR of Application No. 08796246, PCT/US2008/070341, dated May 11, 2012, 6 pages.

Communication under Article 94 of Application No. 08796246, PCT/US2008/070341, dated Jun. 8, 2015, 5 pages.

* cited by examiner

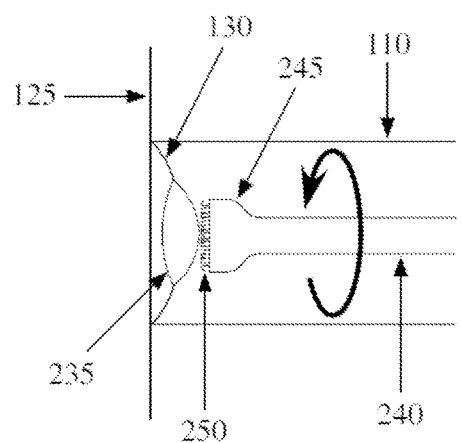
Figure 2C
Figure 2D
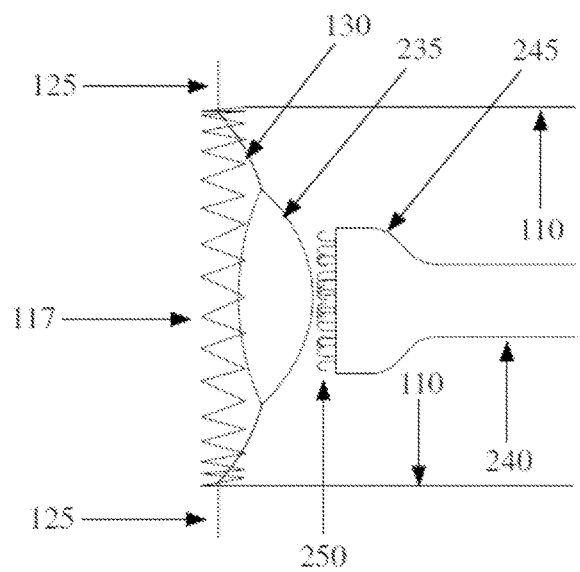

DEVICE AND METHOD OF ORIENTING A BIOPSY DEVICE ON EPITHELIAL TISSUE

FIELD OF THE INVENTION

This invention relates to a device and method of inserting, orienting, retaining and withdrawing a biopsy device to obtain epithelial tissue samples.

BACKGROUND OF THE INVENTION

A lesion is caused by any process that alters or damages tissue. A lesion can be defined as any pathological or traumatic discontinuity of tissue with partial loss of tissue function. The concept of a lesion includes wounds, sores, ulcers, tumors, cataracts and any other tissue damage. Lesions can range from the skin sores associated with eczema to the changes in lung tissue that occur in tuberculosis. Generally, a lesion can be characterized by the epithelium covering the underlying stromal connective tissue becoming fragile, leading to ulceration and bleeding.

Human *papillomaviruses* (HPV) are responsible for many cutaneous and mucosal lesions. Some viral genotypes are considered to be the causal agents of cervical cancer and oropharyngeal cancer. Natural genital HPV infection seems to be poorly immunogenic because of its nonproductive and non-inflammatory characteristics and also because of mechanisms developed by the virus to counteract the immune response. Human epithelial cells may be transformed by insinuation of the viral genome into the nucleus of the cells leading to immortalization of the cells, and neoplastic transformation which can lead to malignancy. Detection of these cellular changes is the aim of cancer screening tests such as the Papanicolaou Smear (Pap smear) of the cervix, which lead to follow up care where special illumination, magnification and the application of acetic acid can reveal visual evidence of cell proliferation. The goal is to find, target, biopsy and ultimately treat true cancer precursor lesions prior to malignant transformation and invasion.

Cervicovaginitis refers to inflammation of the squamous epithelium of the vagina and cervix caused by an inflammatory reaction to an infection. This damage leads to desquamation and ulceration, which can cause a reduction in the epithelial thickness due to loss of superficial and part of the intermediate layers of cells. In the deeper layers, the cells are swollen with infiltration of neutrophils in the intercellular space. The surface of the epithelium is covered by cellular debris and inflammatory mucopurulent secretions. The underlying connective tissue is congested with dilatation of the superficial vessels and with enlarged and dilated stromal papillae. Rare and uncommon cervical infections, due to tuberculosis, schistosomiasis and amoebiasis, cause extensive ulceration and necrosis of the cervix with symptoms and signs mimicking invasive cancer. Herpes simplex virus (HSV) can be present on the mucosal lining of the mouth or genitals. A large coalesced ulcer due to HSV can also mimic the appearance of invasive cancer. Chronic inflammation causing recurrent ulceration and healing of the cervix can result in a distortion of the cervix. Infections with the pathogenic fungi *Cryptococcus neoformans, Histoplasma capsulatum*, and *Coccidioides immitis* can be disseminated and some, e.g., *C. neoformans*, can result in pneumonia or meningitis. Longstanding viral, bacterial, fungal or protozoal infection and inflammation may lead to white or pink appearance as a result of fibrosis.

Previous devices to obtain a biopsy sample include brushes with rigid bristles that puncture and shear epithelial surfaces (U.S. Pat. No. 5,535,756 "Catheter with simultaneous brush cytology and scrape biopsy capability", U.S. Pat. No. 6,258,044 "Apparatus and method for obtaining transepithelial specimen of a body surface using a non-lacerating technique", U.S. Pat. No. 6,494,845 "Retractable brush for use with endoscope for brush biopsy" and U.S. Pat. No. 6,132,421 "Integrated epithelial removal tool"), single metal or plastic curettes that extend in a parallel direction to the applicator handle and are much larger than the innovation (U.S. Pat. No. 4,641,662 "Endocervical curette system" and U.S. Pat. No. 6,730,085 "Surgical biopsy instrument"), scalpels or similar bladed sharp cutting tools (U.S. Pat. No. 5,857,982 "Apparatus and method for removing tissue", U.S. Pat. No. 5,800,362 "Cervical biopsy device", U.S. Pat. No. 3,774,590 "Uterine Specimen Collecting Method", U.S. Pat. No. 5,092,345 "Uterine cell sampler", U.S. Pat. No. 4,061,146 "Tissue macerating instrument", U.S. Pat. No. 5,868,668 "Surgical instrument", U.S. Pat. No. 6,053,877 "Movable sample tube multiple biopsy sampling device", U.S. Pat. No. 5,470,308 "Medical probe with biopsy stylet", U.S. Pat. No. 7,137,956 "Endoscopic submucosal core biopsy device", U.S. Pat. No. 4,168,698 "Endocervical strip biopsy instrument" and U.S. Pat. No. 4,757,826 "Endocervical biopsy instrument"; and U.S. publication No. 2005/0059905 "Tissue extraction and maceration device" and U.S. publication No. 2007/0093727 "Cervical tissue biopsy system and methods of use"), or very large electrified metal loops used to produce excisional biopsies (U.S. Pat. No. 5,913,857 "Methods and devices for collection of soft tissue" and U.S. Pat. No. 5,951,550 "Endocervical conization electrode apparatus"). One device performs simultaneous brush cytology and scrape biopsy on structures with an organic duct (U.S. Pat. No. 5,535,756, "Catheter with simultaneous brush cytology and scrape biopsy capability"). U.S. Pat. No. 5,643,307 "Colposcopic Biopsy Punch with Removable Multiple Sample Basket" has also been proposed to obtain biopsy samples when examining the cervix.

More recently, a number of non bristle biopsy collection devices which utilize a material (e.g., Kylon®) to obtain a biopsy sample from epithelial tissue have been proposed, including U.S. patent application Ser. No. 12/669,638 entitled "Frictional trans-epithelial tissue disruption and collection apparatus and method of inducing and/or augmenting an immune response", which published as U.S. publication No. 20100210968 and Ser. No. 13/072,773 "Frictional trans-epithelial tissue disruption collection apparatus and method of inducing an immune response", which published as U.S. publication No. 20110172557 and which are both explicitly incorporated by reference in their entireties.

Biopsy guides have been used to guide biopsy sampling tools into or onto lesions in the body that require radiological, sonographic, or magnetic resonance imaging, or an endoscopic portal such as a trochar or sheath to penetrate into the body or body cavity to access and accurately aim the active part of the device, usually a needle or cutting forceps tip. The goal of the existing biopsy guide technology has been to guide or target areas that are not easily accessible unless endoscopic or surgical access is provided to reach the target lesion. Biopsy guides are not used for epithelial lesions that are visually apparent outside the body such as skin, in a body cavity easily examined such as the oral cavity, or a body cavity that can be visualized with a speculum such as the vagina or anus.

Often the procedure for obtaining a biopsy sample is complicated when the epithelial tissue lies on an epithelial surface that is moist, wet or laden with mucous or other secretions. Often a biopsy is required of a specific lesion or inflamed region. In these situations, the medical professional will observe a specific location or target from which the biopsy can preferably be sampled. However, one or more procedures including applying, orienting, rotating with applied pressure, excision, obtaining sharp forceps samples with applied pressure and withdrawing the device from the desired specific location can be difficult. Depending on the nature of the epithelial tissue surface being sampled, the mechanical constraints can make these procedures challenging. The surface of female lower genital tract, anal, or oral epithelium may contain keratin or other proteinaceous material, and be coated with secretions from adjacent glands that may contain mucous or saliva. When a brush, fabric, metal forceps or curette is used to remove tissue from the area, the instrument can slide or slip away from a target lesion when pressure is applied to the sampling device, and the examiner can miss the area of concern, and instead sample adjacent "normal" appearing tissue instead. This can lead to examiner sampling error that can provide a false negative result, and missed detection.

SUMMARY OF THE INVENTION

In an embodiment of the invention, a hollow guide is introduced onto a mucosal or non mucosal epithelial surface which can be located on and rest against the desired specific location on the epithelial tissue to be sampled. The sampling device can be inserted into the hollow guide and can be rotated or otherwise manipulated. By applying and retaining the hollow guide on the epithelial tissue, usually guided by landmarks under naked eye visualization, aided magnified view, and with or without special stains applied to the tissue to demarcate lesions, the area in which the sampling device can move is restricted and thereby the sampling device obtains the biopsy sample without moving off the desired specific location. In an embodiment of the invention, by depressing the hollow guide against the epithelial tissue, the epithelial tissue can be forced to bulge thereby presenting a lesion on the epithelial tissue to the sampling device. A flat epithelial surface can have a flat surgical guide or hollow tube applied upon the targeted epithelial area. The bulge occurs because venous egress would be curtailed, creating a more turgid stromal base on which the epithelium is anchored. Frictional or cutting biopsy tools are more likely to strip or excavate the epithelium from a turgid as opposed to a soft depressible surface. Typically, the frictional or cutting biopsy tool would be prevented from invaginating the tissue away from the biopsy tool's active surface. A curved epithelial surface can require the tube be angled to completely surround the lesion and be in contact uniformly and circumferentially. In an embodiment of the invention, the hollow guide can have an acute angle at the end to be rested against the epithelial tissue to allow the surgical guide or hollow tube to be placed at the acute angle relative to the surface of the epithelial tissue. In an alternative embodiment of the invention, the hollow guide can have a right angle at the end resting upon the tissue in order to allow the surgical guide or hollow tube to be placed perpendicular relative to the surface of the epithelial tissue. In an embodiment of the invention, the hollow guide can have a serrated edge at the end to be rested against the epithelial tissue to grip the epithelial tissue. In an embodiment of the invention, the sampling device can be partially withdrawn after sampling and then the hollow guide with the sampling device ensconced within can be completely removed from the tissue surface, thereby ensuring that the biopsy sample is not disturbed by withdrawing the sampling device or that the sampling device take further samples from areas not indicated.

In an embodiment of the invention, a pin guide placed in the center of the sampling device and projecting outwards from the bottom of the sampling device can be applied and inserted into the center of a lesion and function as a fulcrum post to retain the sampling device on a desired location or otherwise to restrict the sampling device from wandering off the desired specific location. The sampling device can be rotated or otherwise manipulated around the pin located on the epithelial tissue.

In various embodiments of the invention, a tissue biopsy sampling device is inserted onto a site within a body cavity or canal within a retention device. In various embodiments of the invention, a tissue biopsy sampling device is located or oriented on a site within a body cavity or canal with a retention device. In various embodiments of the invention, a tissue biopsy sampling device is retained or held in place on a desired specific location on the epithelial tissue with the retention device. In various embodiments of the invention, the epithelial tissue on an external body surface, within a body cavity, on the exposed epithelial surface, a surface of an internal organ, or a surface surrounding a canal is presented to the tissue biopsy sampling device using the retention device. In various embodiments of the invention, a tissue biopsy sampling device is withdrawn from a site within a body cavity, body surface, or canal within the retention device or the retention device is otherwise used to assist withdrawal of the tissue biopsy sampling from within the body surface, cavity or canal.

BRIEF DESCRIPTION OF THE DRAWINGS

The invention is illustrated by way of example and not by way of limitation in the figures of the accompanying drawings in which like references indicate similar elements. This invention is described with respect to specific embodiments thereof. Additional features can be appreciated from the Figures in which:

FIG. 2C is a profile schematic drawing of a hollow guide depressed against epithelial tissue to cause the epithelial tissue inside the surgical guide or hollow tube to bulge and elevate the target lesion and a biopsy sampling device inside the surgical guide or hollow tube being rotated on the lesion according to various embodiments of the invention;

FIG. 2D is an expanded profile schematic drawing of a hollow guide with a serrated edge depressed against epithelial tissue to cause the epithelial tissue inside the surgical guide or hollow tube to bulge and a biopsy sampling device inside the surgical guide or hollow tube in contact with the lesion, according to various embodiments of the invention;

DETAILED DESCRIPTION OF THE INVENTION

Definitions

Figure 1A:
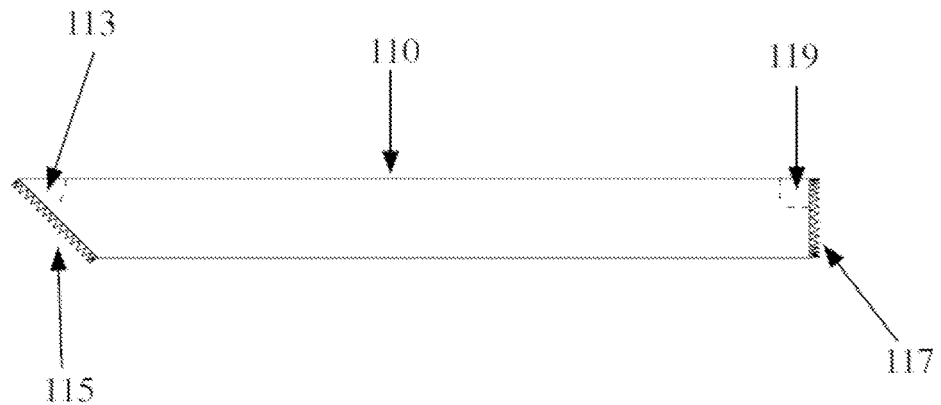
FIG. 1A is a profile schematic drawing of a hollow guide with an acute angle at one end and a right angle at the opposite end, where both edges of the hollow tube are serrated according to various embodiments of the invention.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

As used herein, the phrase "Frictional Tissue Sampling and Collection" (FTSC) device includes bristle brushes with flexible or stiff bristles that buff, sweep and carry away surface cells or puncture and tear away epithelial fragments of multiple layers up to the full epithelial thickness. FTSC devices include trans-epithelial sampling devices using fabric material such as Kylon® to carry away surface cells from the epithelial tissue. FTSC devices also include soft superficial sweeping cytology or rigid or semi-rigid deep epithelial histology sampling brushes that employ bristles.

As used herein, the phrase "outer diameter of the FTSC device" means the outer diameter of the head or any other projection extending from the FTSC device which can restrict the rotation of the FTSC device when inserted into a surgical guide or hollow tube and rotated.

The surgical guide or hollow tube and/or the tissue biopsy device can be made from one or more materials selected from the group consisting of metal coated glass tube, metal coated fused silica tube, machinable glass, metal coated machinable glass, ceramic, metal coated ceramic, plastic, metal coated plastic and metal. Plastics can be made from one or more polymers selected from the group consisting of high impact polystyrene, polyphenylene ether and polystyrene impregnated with pentane, a blend of polyphenylene ether and polystyrene impregnated with pentane or polyethylene, polypropylene, polypropylene/polypropylene composites, polycarbonate, low density polyethylene, high density polyethylene, acrylonitrile butadiene styrene copolymers, polyphenoxy ether alloyed with high impact polystyrene, polyether, polyglycol, polyester, polyethylene, poly(halogen)ethylene, polypropylene, polyvinylidene halogen, polymethylmethacrylate, polyacrylonide, polycaprolactone, polylactide, poly butylene succinate, polybutylene succinate adipate, polybutylene succinate terephthalate, poly-hydroxypropionate, poly-hydroxybutyrate, poly-hydroxyvalerate, poly-hydroxyhexanoate, poly-3-hydroxyoctanoate, poly-3-hydroxyphenylvaleric acid and poly-3-hydroxyphenylhexanoic acid.

In the following description, various aspects of the present invention will be described. However, it will be apparent to those skilled in the art that the present invention may be practiced with only some or all aspects of the present invention. For purposes of explanation, specific numbers, materials, and configurations are set forth in order to provide a thorough understanding of the present invention. However, it will be apparent to one skilled in the art that the present invention may be practiced without the specific details. In other instances, well-known features are omitted or simplified in order not to obscure the present invention.

Various operations will be described as multiple discrete steps in turn, in a manner that is most helpful in understanding the present invention; however, the order of description should not be construed as to imply that these operations are necessarily order dependent.

Various embodiments will be illustrated in terms of exemplary classes and/or objects in an object-oriented programming paradigm. It will be apparent to one skilled in the art that the present invention can be practiced using any number of different classes/objects, not merely those included here for illustrative purposes. Furthermore, it will also be apparent that the present invention is not limited to any particular software programming language or programming paradigm.

It should be noted that references to 'an' or 'one' embodiment in this disclosure are not necessarily to the same embodiment, and such references mean at least one.

The following issued U.S. patents and published applications disclose devices, applications or procedures which can benefit from the proposed invention, U.S. Pat. Nos. 3,789,852; 4,177,797; 4,619,829; 4,699,154; 4,716,901; 4,781,202; 4,785,826; 4,899,729; 4,958,625; 5,053,396; 5,056,529; 5,183,464; 5,282,476; 5,320,611; 5,496,827; 5,526,822; 5,814,632; 5,912,272; 5,945,420; 5,976,844; 5,984,930; 6,183,761; 6,248,763; 6,440,949; 6,918,881; 6,926,677; 7,087,028; 7,309,317; 7,658,718; 7,828,748; 7,988,642; 8,096,956; 8,167,819; D422,706; RE34,056; and U.S. publication No. 2003/0225343 and U.S. publication No. 2009/0318830.

A trans-epithelial Frictional Tissue Sampling and Collection (FTSC) device can be used to perform biopsies of lesions suspected of harboring disease. Clinicians are used to a rotational soft bristle brush to collect endocervical cytology. This soft bristle brush is rotated, with the soft bristles removing superficial cells. When a deeper biopsy is required after an abnormal pap smear or to evaluate the cause of vaginal bleeding, clinicians currently use a sharp edge curette. A sharp edge curette is not designed to and customarily is not rotated to obtain a biopsy. Instead, it is repeatedly inserted, then withdrawn against the canal beginning at a reference point. As the cervix is cylindrical with a circular face, the clinician typically starts at a reference point, usually 12:00 o'clock position, and shift, rotating to all positions around the clock, sequentially back and forth rotated as it is pushed in and pulled back. A clinician can use the sharp curette, most commonly as the Kevorkian curette, and scrape the cervical os surface to accumulate cells. The to and from scraping motion shears epithelium and cells which lie free in the canal and are later collected, as the curette is not also designed to collect the majority of tissue harvested. The procedure with the Kevorkian curette is both painful and can cause trauma to the cervix, as it shaves and detaches the epithelium from the underlying stroma. A cylindrical or tapered stiff bristle brush could also be used, but would also prove resistant to entry if there was a tight fit, potentially causing pain and trauma. It should be noted that an instrument, once inserted and secured within a tight fitting canal, may not migrate from the target biopsy area, especially if the target area is the entire endocervical canal, as the curette is recessed into and secured in the endocervical canal during the curettage method.

When a curette or instrument is placed in a canal like structure or duct, the tubular shape of the canal can steady the instrument during manipulation, preventing migration away from the canal target area. In some epithelial surfaces prone to neoplastic transformation, like the cervix, the area around the entry point to the endocervical canal or the distal portion of the canal near the entry point is the most likely location for neoplastic transformation and progression towards malignancy. The surface circumferentially located around the endocervical opening or "os" is also called the transformation zone or squamocolumar junction. It is the likely site of cervical neoplasia noted after abnormal Pap smear cytological evidence in screening and when examined visually with the naked eye or colposcopic magnification on the exocervix or portio, likely to be the site of neoplastic lesions that appear white and may have abnormal vasculature after the application of acetic acid. Currently, such lesions are the target of forceps biopsy, brush biopsy, fabric based biopsy, electrothermal excision, or other sharp excision or curettage sampling techniques. The biopsy evidence is used to guide ultimate therapy, so accurate targeting and removal of tissue evidence of such targets is paramount in importance. Any ancillary instrument that will steady the biopsy device and prevent slippage, wandering, mis-targeting, or migration from the lesion will improve the quality of the procedure and its accuracy. In addition, if the device not only isolates the lesion and maintains the device to its location, but also physically alters the lesion making it more accessible to removal, a deeper and more representative sample is possible.

Figure 1B:
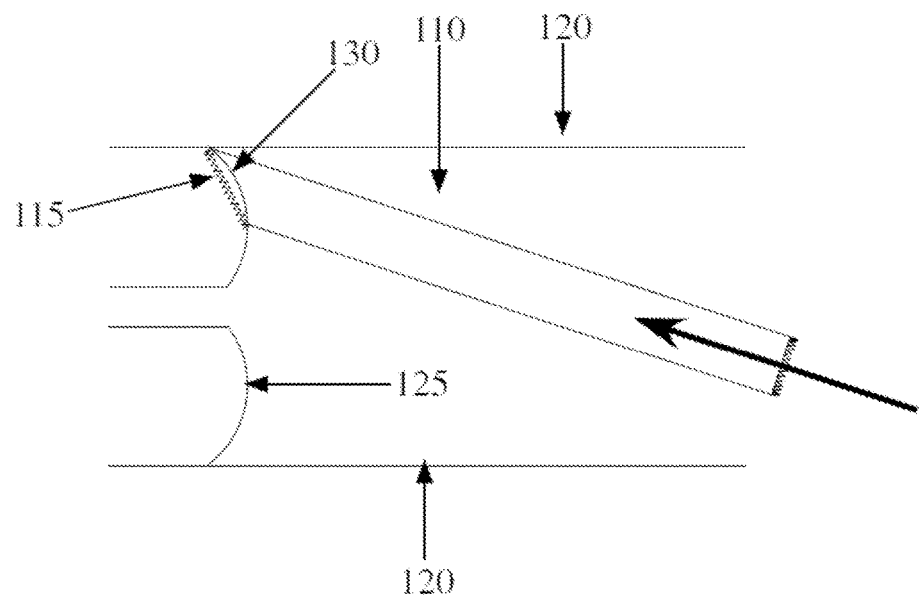
FIG. 1B is a profile schematic drawing of the hollow guide shown in FIG. 1A where the serrated edge of the acute angle end of the surgical guide or hollow tube is depressed from one side against the epithelial tissue surface such as the cervix contiguous with the uterus according to various embodiments of the invention.
Figure 1C:
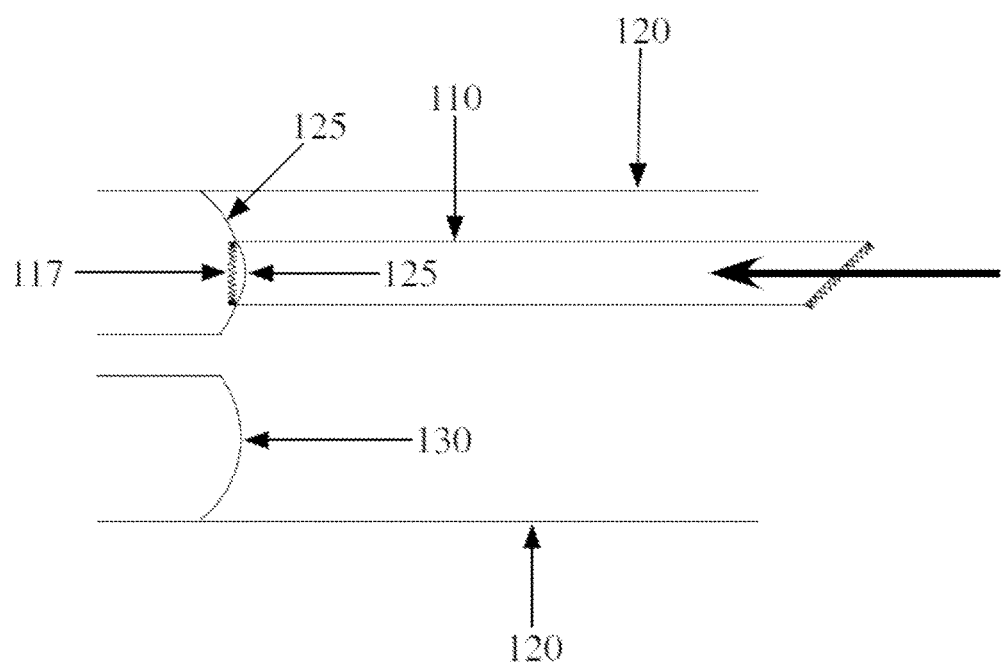
FIG. 1C is a profile schematic drawing of the hollow guide shown in FIG. 1A where the serrated edge of the right angle end of the surgical guide or hollow tube is directly depressed against the epithelial tissue such as the cervix, or the oropharynx, the anus, or similar epithelium surfaces according to various embodiments of the invention.

Currently a clinician can choose an exo-cervical FTSC or an endo-cervical FTSC biopsy tool. The biopsy guide cylinder of the surgical guide is pressed against the tissue, with the serrations preventing the biopsy guide cylinder, and thereby the FTSC, from sliding around. As a result, the FTSC stays on target. The biopsy guide cylinder is not a sheath, that intentionally covers the tip of the biopsy or sampling area protecting it from contamination. The biopsy guide cylinder is not a trochar, that allows passage like a tunnel between areas of the body. In an embodiment of the invention, the surgical guide prevents migration or sliding of the FTSC device from the lesion. In one embodiment of the invention, the surgical guide is transparent to allow continued visualization of the application of the biopsy or sampling device to the target lesion. In an alternative embodiment of the invention, a clinician can choose a surgical guide in which to one or more introduce, shield, position, retain retract, withdraw the FTSC screening biopsy tool. As shown in FIG. 1A in an embodiment of the invention, the clinician can choose between depressing the serrated acute angle end 115, or the serrated right angle end 117 of the hollow surgical guide or biopsy guide cylinder 110 against the epithelial tissue. In an embodiment of the invention, the serrated edge can be used to hold the tube in place on the epithelial tissue. In an alternative embodiment of the invention, a non serrated edge hollow surgical guide can be held in place by applying greater force to the surgical guide 110 on the epithelial tissue (not shown) and thereby increase the resistance to slippage or shifting of the surgical guide 110 on the epithelial tissue (not shown). The end with a flat (or right angle 119) profile 117, can be used when the epithelial tissue can be accessed by placing the tube at approximately a right angle to the tissue, e.g., from directly above. The end with a beveled (or acute angle 113) profile 115, can be used when the epithelial cannot be accessed from directly above. In various embodiments of the invention, a clinician can chose between surgical guides with acute angle cuts of 15, 30, 45, 60 and 75 degree cuts. In various embodiments of the invention, hollow surgical guides with angles between 5 degrees and 85 degrees can be used to produce differing profile hollow surgical guide ends. As shown in FIG. 1B in an embodiment of the invention, in contrast to a proximal epithelial surface 125, a distal epithelial surface 130 within a canal 120 can best be approached from an angle using the acute end 115 of the surgical guide 110. As shown in FIG. 1C in an embodiment of the invention, in contrast to a distal epithelial surface 130, a proximal epithelial surface 125 within a canal 120 can best be approached from the normal using the right angle end 117 of the surgical guide 110. The arrows in FIG. 1B and FIG. 1C show the end used to access the surgical guide 110 and the direction of insertion of the FTSC device (not shown). In an alternative embodiment of the invention, the perpendicular or angled ends can be curved in a convex or concave shape to match the curvature or the slope of the tissue to which the surgical guide 110 is applied.

Figure 2A:
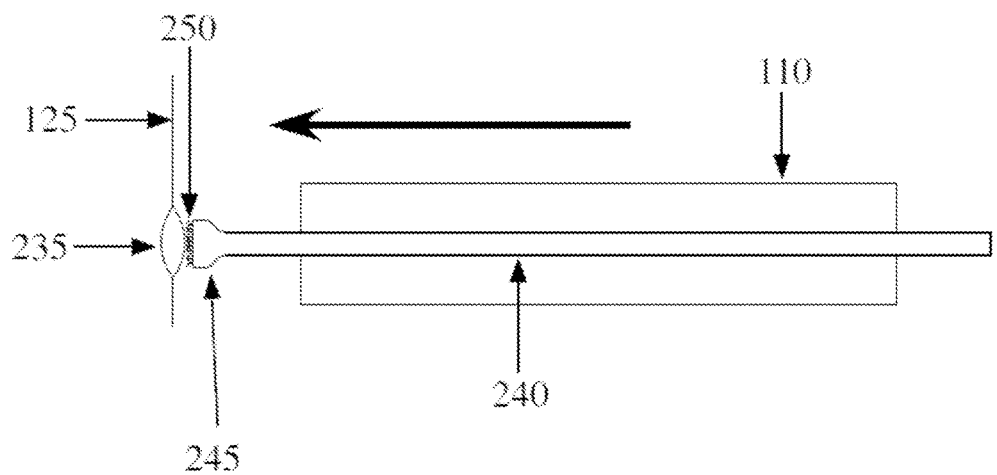
FIG. 2A is a profile schematic drawing of a hollow guide with a biopsy sampling device inserted through the surgical guide or hollow tube in contact with a lesion on epithelial tissue according to various embodiments of the invention.

As shown in FIG. 2A in an embodiment of the invention, the clinician can choose to first apply the tissue extracting means 250 extending from the head 245 of the FTSC device 240 to a particular site or lesion 235 of the epithelial surface 125 and subsequently moving the surgical guide 110 over the head 245 of the FTSC device 240 (in the direction of arrow). In an alternative embodiment of the invention, the surgical guide 110 can first be located to cover a particular site or lesion 235 of the epithelial surface 125 and then the FTSC device 240 can be inserting through the surgical guide 110 so that the tissue extracting means 250 extending from the head 245 of the FTSC device 240 contacts the particular site or lesion 235 (not shown schematically). In another embodiment of the invention, the surgical guide 110 and FTSC device can be locked in place to enable insertion in unison to allow the surgical guide to protect the tissue extracting means 250. Once the surgical guide 110 is in position surrounding the site of interest 235, the FTSC device 240 can be unlocked from the surgical guide 110 and pushed down onto the site of interest 235.

Figure 2B:
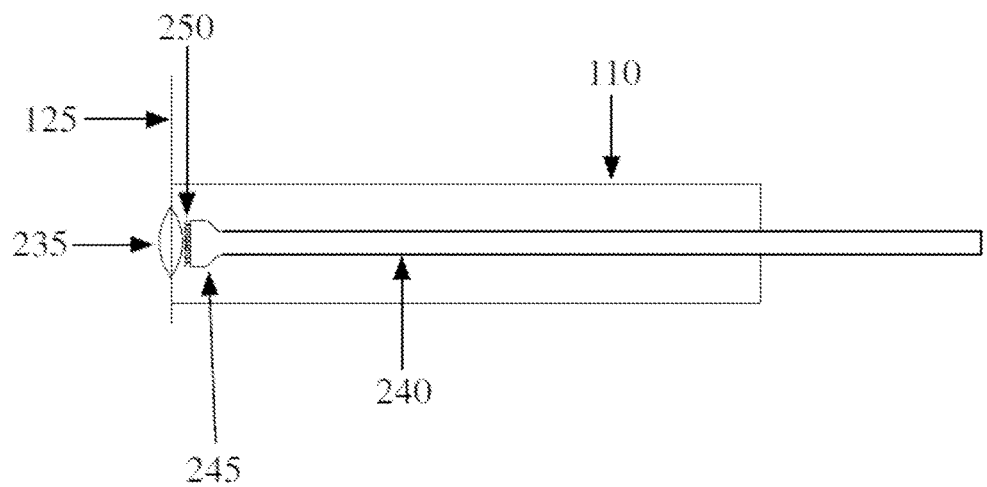
FIG. 2B is a profile schematic drawing of a hollow guide with a biopsy sampling device inserted through the surgical guide or hollow tube in contact with a lesion on epithelial tissue where the surgical guide or hollow tube has been depressed against the epithelial tissue according to various embodiments of the invention.

As shown in FIG. 2B in various embodiments of the invention once the FTSC device 240 and the surgical guide 110 are in position over the particular site or lesion 235 of the epithelial surface 125 the surgical guide 110 can be used to constrain the tissue extracting means 250 extending from the head 245 of the FTSC device 240 from moving off particular site or lesion 235. As shown in FIG. 2C in various embodiments of the invention once the FTSC device 240 and the surgical guide 110 are in position over the particular site or lesion 235 of the epithelial surface 125 the FTSC device 240 can be rotated (as shown with arrow) to allow the tissue extracting means 250 extending from the head 245 of the FTSC device 240 to take epithelial tissue samples from the particular site or lesion 235. As shown in FIG. 2D in various embodiments of the invention once the FTSC device 240 and the surgical guide or hollow tube 110 are in position over the particular site or lesion 235 of the epithelial surface 125 the surgical guide 110 can be depressed to make the right angle end 117 of the surgical guide 110 grip and secure the surgical guide 110 at the particular site to insure the tissue extracting means 250 extending from the head 245 of the FTSC device 240 to take epithelial tissue samples from the particular site or lesion 235.

In various embodiments of the invention once the FTSC device 240 and the surgical guide or hollow tube 110 are in position over the particular site or lesion 235 of the epithelial surface 125 the surgical guide or hollow tube 110 can be depressed to make the particular site 235 bulge and become more accessible to the FTSC device 240.

Figure 2E:
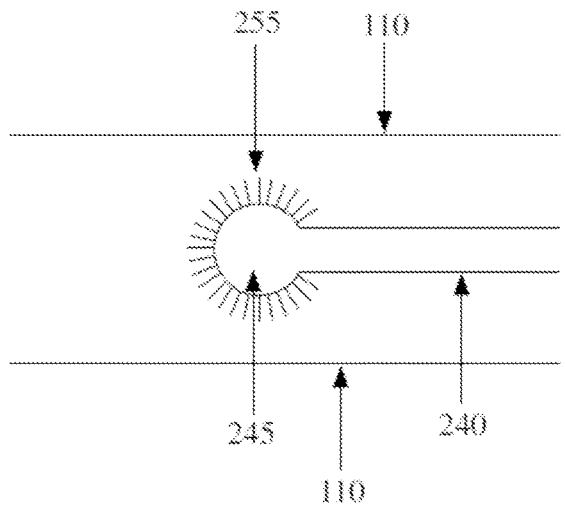
FIG. 2E is an expanded profile schematic drawing of a hollow guide with a bristle brush biopsy sampling device inside the surgical guide or hollow tube which can be used to contact a lesion according to various embodiments of the invention.

As shown in FIG. 2E in various embodiments of the invention the FTSC device 240 inserted into the surgical guide or hollow tube 110 can be of a variety of different geometries including a spherical head 245 with bristles as the extracting means 255 extending from the spherical head 245 to take epithelial tissue samples from the particular site or lesion 235. The FTSC device 240 can be rotated to allow the tissue extracting means 255 extending from the specifically shaped head 245 (e.g., trumpet shaped head with flat platform, or flat spiral coil of the stiff bristle brush, ETC) of the FTSC device 240 to take epithelial tissue samples from the particular site or lesion.

In an embodiment of the invention, the surgical guide or hollow tube 110 can have an inner diameter of approximately 5 mm and the FTSC device 240 can have an outer diameter of approximately 2 mm. In an embodiment of the invention, the FTSC device 240 can have an outer diameter of approximately 4 mm. In an alternative embodiment of the invention, the surgical guide or hollow tube 110 can have an inner diameter of approximately 25 mm and the FTSC device 240 can have an outer diameter of approximately 18 mm. In an embodiment of the invention, the FTSC device 240 can have a diameter of approximately 23 mm.

Figure 2F:
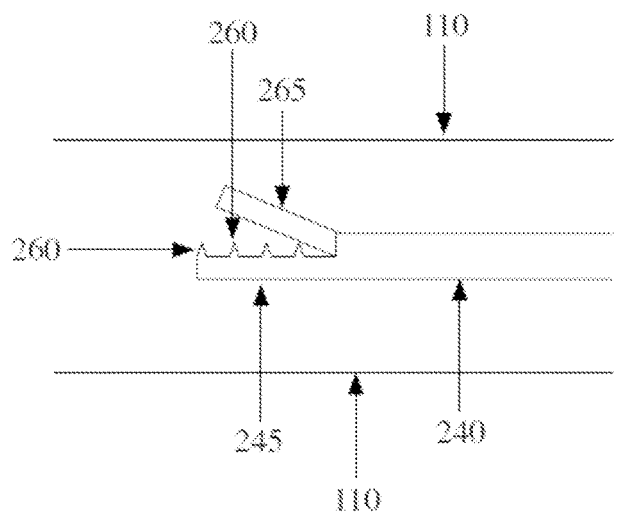
FIG. 2F is an expanded profile schematic drawing of a hollow guide with an opposing jaw forceps biopsy sampling device inside the surgical guide or hollow tube which can be used to contact a lesion according to various embodiments of the invention.

As shown in FIG. 2F in various embodiments of the invention the FTSC device 240 can be inserted into the surgical guide or hollow tube 110 and can have one or more moveable jaws 245, 265 with teeth 260 that become exposed on a jaw 245. The FTSC device 240 can be rotated to allow the tissue extracting means 260 extending from the jaw 245 of the FTSC device 240 to take epithelial tissue samples by grasping, punching, excising, and otherwise capturing tissues within the jaws of the forceps from the particular site or lesion.

Figure 3A:
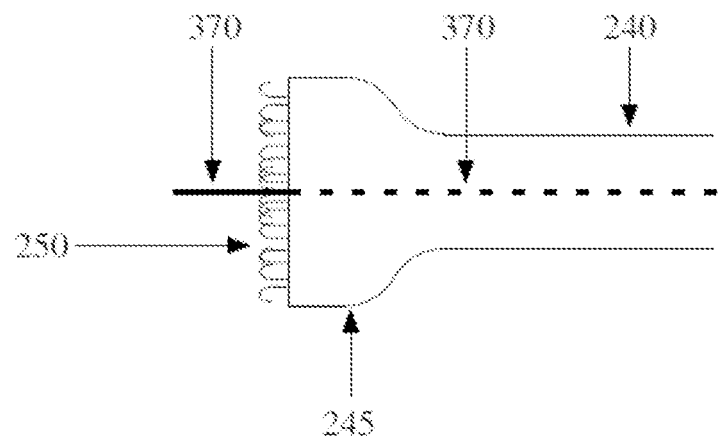
FIG. 3A is a profile schematic drawing of a biopsy sampling device with a central pin which can contact a lesion on epithelial tissue according to various embodiments of the invention.
Figure 3B:
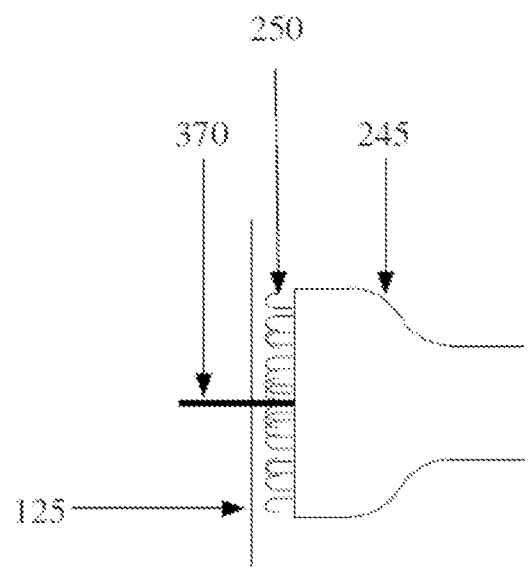
FIG. 3B is a profile schematic drawing of a biopsy device with a central pin in contact with epithelial tissue according to various embodiments of the invention.

As shown in FIG. 3A in an alternative embodiment of the invention, the head 245 with a central pin 370 of the FTSC device 240 can be used to retain the FTSC device 240 on the site of interest 235. As shown in FIG. 3B, the central pin 370 can insert into the epithelial tissue 125 to insure that the sampling means 250 extending from the head 245 samples from the particular site or lesion.

Figure 4A:
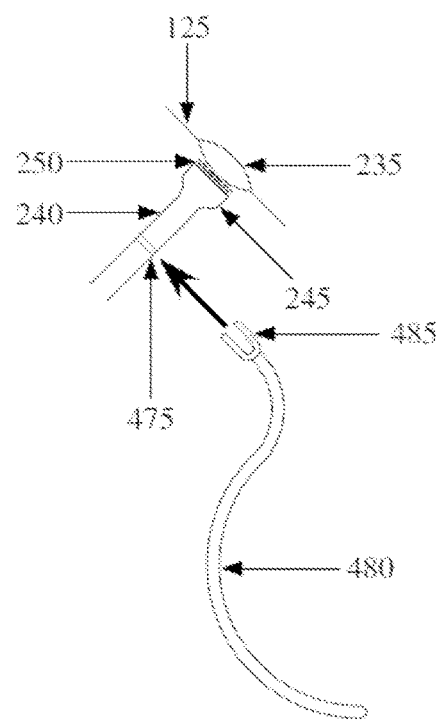
FIG. 4A is a profile schematic drawing of a biopsy device with a collar and an attachable cantilever arm which can be used to retain the biopsy device on a specific epithelial tissue location while the biopsy device is rotated according to various embodiments of the invention.
Figure 4B:
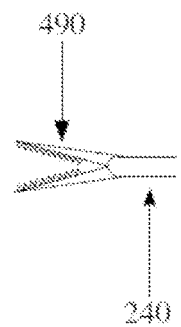
FIG. 4B is a profile schematic drawing of an alternative configuration of a biopsy sampling device to that shown in FIG. 4A suitable for use with one or more of the various embodiments of the invention.
Figure 4C:
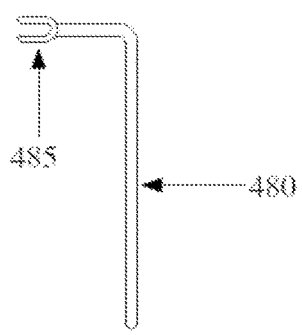
FIG. 4C is a profile schematic drawing of an alternative configuration of an attachable cantilever arm to that shown in FIG. 4A suitable for use with one or more of the various a biopsy sampling device according to various embodiments of the invention.

As shown in FIG. 4A in another embodiment of the invention, the FTSC means 250 extending from the head 245 can be retained on the lesion 235 of the epithelial tissue 125 by inserting a cantilever arm 480 into a receptacle 475 on the FTSC device 240. The cantilever arm 480 can be used by the clinician to insure that the sampling means 250 extending from the head 245 does not wander off the lesion 235 with rotation of the tissue sampling device. FIG. 4B shows an alternative configuration of a FTSC device 240 with two jaws 490 that open to expose serrated edges suitable for use with one or more of the various embodiments of the invention. FIG. 4C shows an alternative configuration of an attachable cantilever arm suitable for use with the FTSC device described in FIG. 4A according to various embodiments of the invention.

Figure 5A:
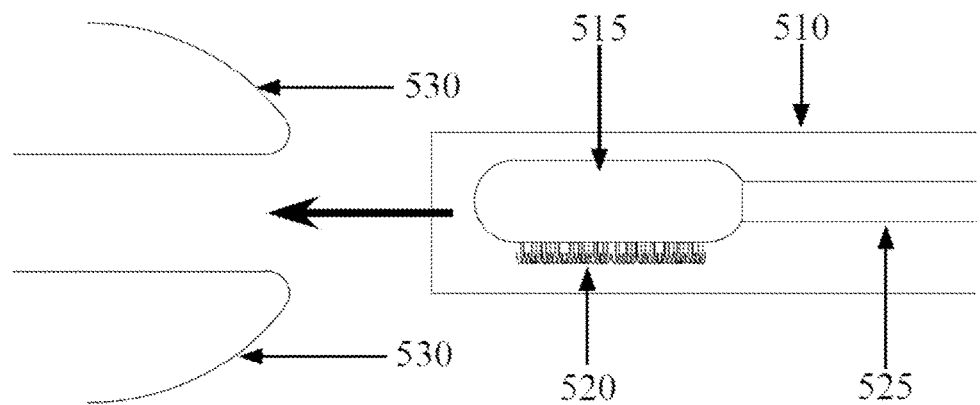
FIG. 5A is a profile schematic drawing of an ensheathed head of a frictional transepithelial device approaching a cervical canal orifice according to various embodiments of the invention.
Figure 5B:
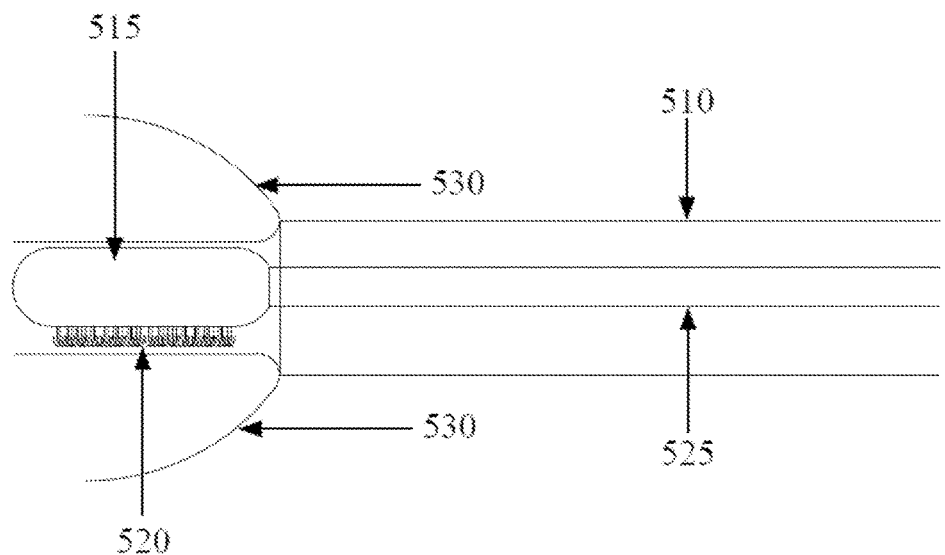
FIG. 5B is a profile schematic drawing of a head of a frictional transepithelial device inserted into a canal structure with the sheath remaining external according to various embodiments of the invention.

FIG. 5A shows a hollow tube or guide which also functions as a sheath 510 with a FTSC device 525 located inside and the FTSC device 525 having a head 515 and an extracting means 520. The FTSC device 525 is about to be inserted in the cervical canal 530. FIG. 5B shows the head 515 of the FTSC device 525 inserted into the cervical canal 530 and ready to extract tissue for sampling while the sheath 510 remains on the outside of the canal opening as a barrier to the abrasive surface extracting means 520. The sheath serves as a guide for the FTSC device 525 to accurately enter the orifice in the canal 530 without deflection or straying or contacting the entry or portio of the canal surface which prevents contamination of the canal epithelium 530 with external tissue during frictional rotation. In an alternative embodiment of the present invention (not shown), the sheath is inserted into the canal along with the head of the device and then later withdrawn so the FTSC device is then in direct contact with the walls of the endocervical canal.

Figure 6A:
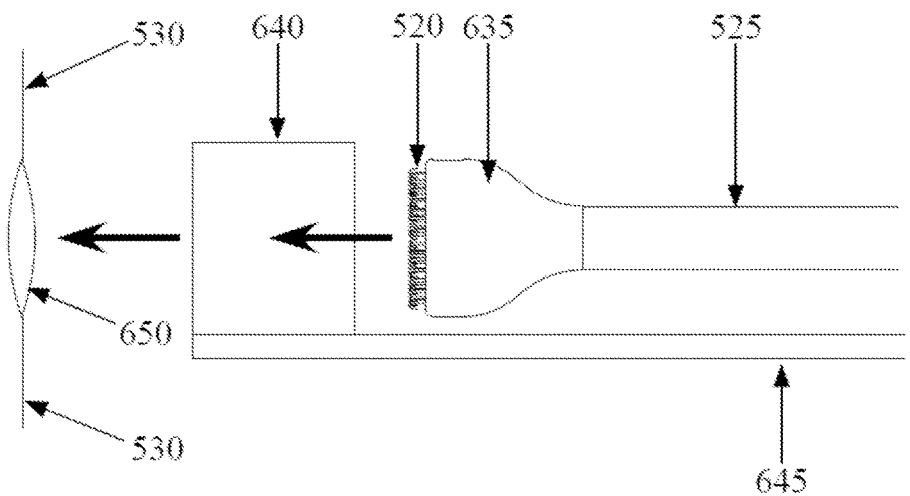
FIG. 6A is a profile schematic drawing of a frictional tissue sampling and collection device approaching a target lesion on a flat or curved tissue plane with a cylindrical biopsy guide in advance of the device according to various embodiments of the invention.
Figure 6B:
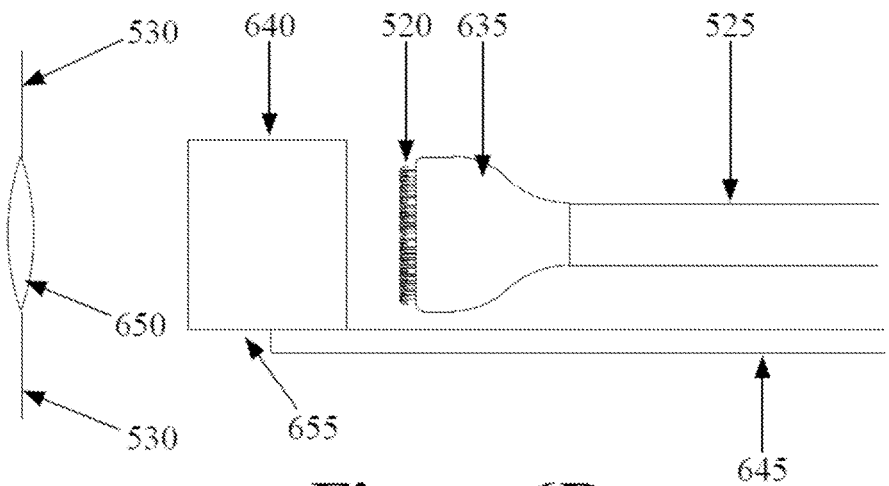
FIG. 6B is a profile schematic drawing of a frictional tissue sampling and collection device with a ring or guide in advance of the device according to various embodiments of the invention.
Figure 6C:
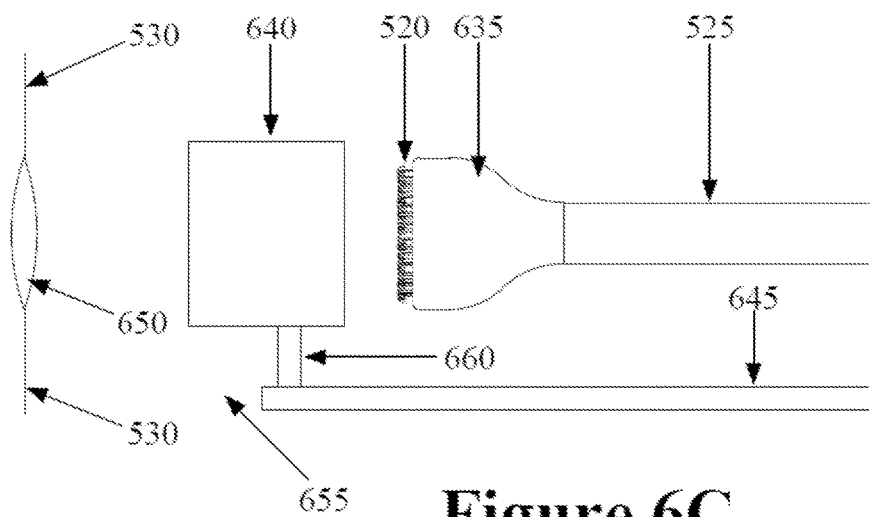
FIG. 6C is a profile schematic drawing of a frictional tissue sampling and collection device with a ring or guide offset from the device and connected by a bridge or post according to various embodiments of the invention.
Figure 6D:
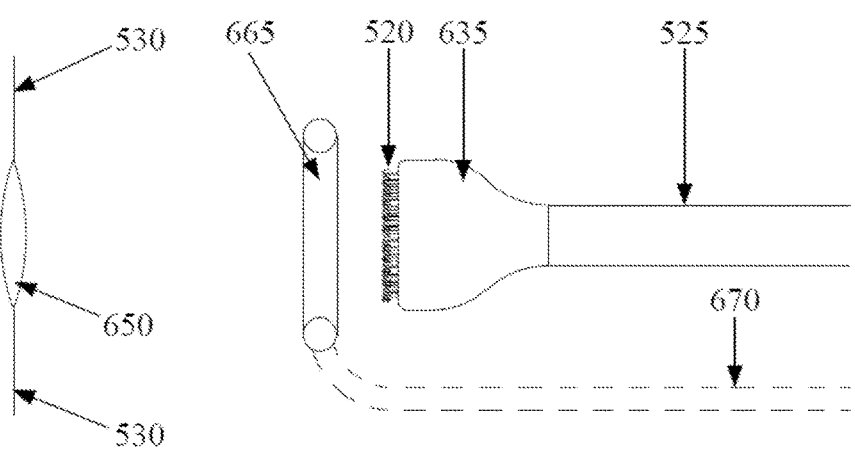
FIG. 6D is a profile schematic drawing of a frictional tissue sampling and collection device with a ring or guide connected by a curved angle joint at the device according to various embodiments of the invention.
Figure 6E:
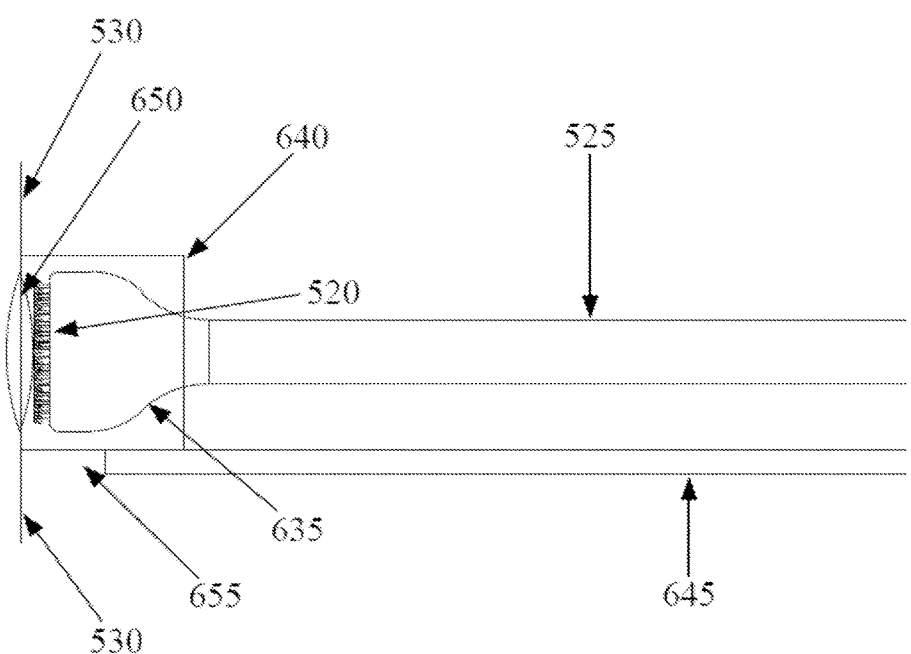
FIG. 6E is a profile schematic drawing of a frictional tissue sampling and collection device at a target lesion according to various embodiments of the invention.

Oral biopsies, cervical vaginal, perianal biopsies are all visualized directly, not endoscopically. Therefore, these procedures do not involve an endoscopic trochar or sleeve. As such, placing a surgical guide or hollow tube over the devices used to sample tissue for these biopsies in order to support, guide, and maintain the FTSC devices on the tissue is novel and non-obvious. Such surgical guides can also expose or bulge epithelial lesions and make them more amenable to excisional biopsy as well and may prove useful in that regard. Surgical steel or metal is customarily used for punch biopsy forceps and similar devices and application on smooth slippery epithelium may cause sliding or skating to occur when the sharp edge contacts squeezes, and pinches the target lesion. By creating a perimeter or barrier, such sliding will be prevented and a more accurate biopsy enabled. Accordingly, the invention is considered to be especially useful for "external" biopsy guidance on the surface, as shown in FIGS. 6A-E and FIG. 7A-B, especially mucosal surfaces prone to mucous production or moisture and those which can be keratinized, including the vulva, vagina, cervix, oral cavity, and anus. In an embodiment of the invention, as shown in FIGS. 6A-C, a FTSC device 525 approaches a lesion 650 with a cylindrical biopsy guide 640 in advance of the FTSC device 525. FIG. 6A shows the surgical guide 640 flush with the probe 645. FIG. 6B shows the surgical guide 640 offset from the probe 645 with a gap 655 between the distal shaft of the probe 645, the surgical guide 640 and the tissue face of the canal 530. In FIG. 6C, the surgical guide 640 is connected by a bridge or post 660 to the probe 645 with a gap 655 between the distal shaft of the probe 645, the surgical guide 640 and the tissue face of the canal 530. FIG. 6D shows an alternative embodiment of the invention. The surgical guide 665 is flatter and curved in shape as well as connected by the curved angle joint at the distal probe 670. As shown in FIGS. 6A-E, the surgical guide 645 surrounds the target lesion 650, and with pressure as shown in FIG. 6E, the tissue of the canal 530 inside the cylindrical tube bulges slightly, exposing the epithelial layer making it more accessible to the surface abrasion or excavation means 520 of the FTSC device (e.g., fabric, bristle brush, or cutting tool) 525.

In an embodiment of the invention, as shown in FIG. 6, the surgical guide 645 prepares the tissue of the canal 530 for the FTSC device 525. In an embodiment of the invention, as shown in FIG. 6E, the pressure applied to the biopsy guide cylinder 640 makes the tissue of the canal 530 inside the cylinder 640 'plump', exposing the epithelial lesions 650 that are folded into crevices, making for easier excavation, excision, or abrasion to completely remove the lesion 650.

Figure 7A:
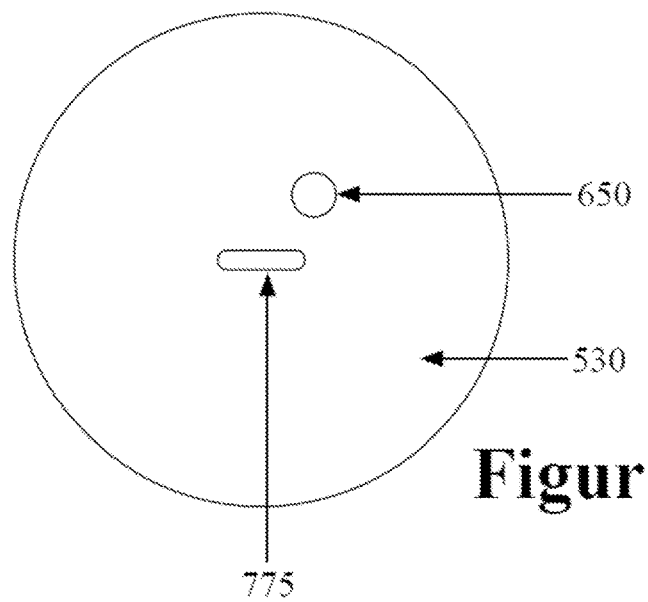
FIG. 7A is a schematic drawing of the target lesion inside the canal as visualized by the user and with the target on exocervix according to various embodiments of the invention.
Figure 7B:
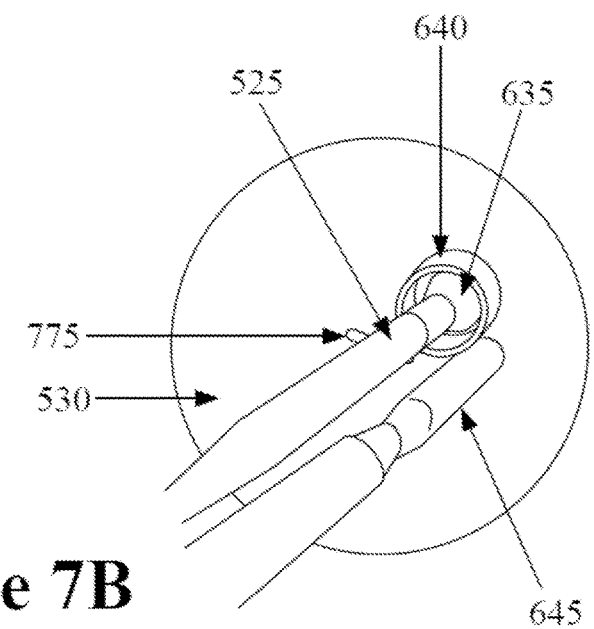
FIG. 7B is a schematic drawing of biopsy guide pressed on lesion as visualized and circumferentially placed so the center of lesion is in the center of ring with pressure, causing the center of epithelium to bulge up according to various embodiments of the invention.

The biopsy guide cylinder 640 symmetrically depresses the tissue 530 around the lesion 650 to extrude it or make it bulge forward. Accordingly, the appropriate angle to allow access to the lesion 650 can be reached without the need for additional instruments or cotton applicators to manipulate the tissue angle exposed or surface contour exposed. In addition, the turgidity of the lesion 650 increases as bulging tissue is firmer. FIG. 7A shows a view of the clinician who is viewing the exocervix 775 and targeting a lesion 650 on the epithelial tissue in the canal 530. FIG. 7B shows a probe 645 under the FTSC device 525 with a cylindrical biopsy guide 640 near the head 635 of the FTSC device 525.

In an embodiment of the invention, the surgical guide provides a firmer more turgid base because the blood vessels/capillaries underneath the epithelial tissue are temporarily tamponaded or occluded, causing it to prevent venous drainage from the tissue under the cylinder. Frictional, lacerational, or pure cutting requires the tissue to have some tensile strength, and not to simultaneously depress when the surface is pressed. Pinching jaw type forceps or cutting tools like the gynecological punch biopsy forceps, will be assisted by the "plumping". In an embodiment of the invention, some plumping is required, but not excessive plumping. Accordingly, the pressure on the biopsy guide cylinder can be reduced, to allow some folding or depression of the tissue so the forceps can grasp a fold of the epithelium in the jaws, pinch it off, and excise the piece of intact tissue (e.g., like two shovel spades excavating a piece of sod from lawn).

In an embodiment of the invention, if the cylinder is pressed hard enough, it will reduce the arterial flow to the area and reduce the immediate bleeding. Accordingly, the surgical guide can produce a less traumatic biopsy. So this tamponade effect reduces bleeding with pressure. In an embodiment of the invention, a hemostatic intervention can be carried out immediately after the FTSC biopsy. In an embodiment of the invention, after withdrawing the FTSC device a chemical cauterization is carried out using application of silver nitrate stick (e.g., a styptic pencil) to lesion or ferric sub-sulfate (Monsel's Solution), or cautery, while the pressure tamponade is being applied. By keeping the FTSC area within the biopsy guide cylinder dry, the cauterizing process can be more efficient. Thus, the tamponade caused by the biopsy guide cylinder pressure makes for easier hemostatic management.

Solutions such as Monsel's solution can be caustic and irritating to tissues surrounding the bleeding biopsy site. The biopsy guide can also serve as a conduit to inject the solution, or place a cotton swab coated with solution or gel and limit its application to the bleeding site or wound, and prevent spread of the solution or gel to normal adjacent tissues.

In an embodiment of the present invention, Radio Frequency IDentification (RFID) tag is embedded in one or both of the tissue sampling and the surgical guide or hollow tube. In an embodiment of the present invention, a charge-coupled device (CCD) camera is embedded in one or both of the FTSC device and the surgical guide or hollow tube. The approximate position of the FTSC device and the surgical guide or hollow tube can then be detected through a combination of RFID location and camera detection. In an embodiment of the invention, the FTSC device and the surgical guide or hollow tube are automatically dispensed by an apparatus that recognizes the RFID tag in the FTSC device and the surgical guide or hollow tube. In an embodiment of the invention, the RFID tag is used to identify the characteristics (angle and edge nature) of the surgical guide or hollow tube being supplied. In an embodiment of the invention, the RFID tag is used to identify the characteristics of the FTSC device being supplied. In one embodiment of the invention, the RFID tag operates using an Ultra High Frequency (UHF) signal. In another embodiment of the invention, the RFID tag operates using a microwave frequency signal.

In one embodiment the RFID tag is read only. In another embodiment, the RFID tag contains an Electrically Erasable Programmable Read-Only Memory (EPROM), which enables both read and write functions. In an embodiment of the invention, the RFID tag is passive. In another embodiment of the invention, the RFID tag is semi passive containing a source of energy such as a battery to allow the tag to be constantly powered. In a further embodiment of the invention, the RFID tag is active, containing an internal power source, such as a battery, which is used to power any Integrated Circuits (ICs) in the tag and generate the outgoing signal. In another embodiment, the tag has the ability to enable location sensing through a photo sensor.

In one embodiment of the invention, means of communication with a base station is embedded in one or both the FTSC device and the surgical guide or hollow tube.

In one embodiment of the invention, the communication means utilizes one or more of a wireless local area network; a wireless wide area network; a cellular network; a satellite network; a Wi-Fi network; and a pager network. In one embodiment of the invention, a modem capable of communicating with one or more of the aforementioned networks is embedded in one or both the FTSC device and the surgical guide or hollow tube. In the following discussion the term 'cellular modem' will be used to describe the device embedded. The term 'cellular modem' will be herein used to identify any device of comparable size capable of communicating over one or more of the aforementioned networks. In one embodiment of the invention, the cellular modem can be a Code Division Multiple Access (CDMA) modem. In an embodiment of the invention, a RFID reader and associate integrated circuit processor can be embedded together with the cellular modem in one or both the FTSC device and the surgical guide or hollow tube. In such an embodiment, the RFID tags and RFID reader can be positioned to optimize the RFID read of the RFID tags.

In an embodiment of the invention, the RFID reader and associate processor can be in communication with the cellular modem. In an embodiment of the invention, the cellular modem is in communication with a base station and can transmit one or more parameters selected from the group consisting of one or more RFID tag location, one or more RFID tag identification code, canal type, patient, diagnosis and time stamp.

In one embodiment of the invention the RFID code uses the IEEE format and is Electronic Product Code (EPC) readable. In another embodiment of the invention the RFID code uses the Uniform Commercial Code (UCC) format and is Universal Product Code (UPC) readable. In another embodiment, the format is compatible for EPC, European Article Number (EAN) and UPC read and write functions.

In an embodiment of the invention, the device method or system can be used for the treatment of humans. In an embodiment of the invention, the device method or system can be used for the treatment of animals. In an embodiment of the invention, the device method or system can be used in veterinary applications. In an embodiment of the invention, the device method or system can be used in medical applications.

The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.

ASPECTS OF THE INVENTION

Some aspects of this invention include a method of obtaining a tissue biopsy comprising the steps of directing a surgical guide adjacent to or inside a body cavity onto an epithelial surface, where the surgical guide is adapted to be held in place on the epithelial tissue; inserting the tissue biopsy device within the surgical guide; sampling with the tissue biopsy device; and withdrawing the tissue biopsy device from the surgical guide.

Other aspects include a method of obtaining a tissue biopsy comprising the steps of directing a surgical guide adjacent to or inside a body cavity onto an epithelial surface, where the surgical guide is adapted to be held in place on the epithelial tissue; inserting the tissue biopsy device within the surgical guide; sampling with the tissue biopsy device; and withdrawing the tissue biopsy device from the surgical guide, further comprising using one or more alignment stops associated with one or both the surgical guide and the tissue biopsy device to allow the tissue biopsy device to remain partially inserted or fully inserted into the surgical guide during one or more of steps.

Other aspects include a method of obtaining a tissue biopsy comprising the steps of directing a surgical guide adjacent to or inside a body cavity onto an epithelial surface, where the surgical guide is adapted to be held in place on the epithelial tissue; inserting the tissue biopsy device within the surgical guide; sampling with the tissue biopsy device; and withdrawing the tissue biopsy device from the surgical guide, where sampling with the tissue biopsy device includes rotating the tissue biopsy device within the surgical guide.

Other aspects include a method of obtaining a tissue biopsy comprising the steps of directing a surgical guide adjacent to or inside a body cavity onto an epithelial surface, where the surgical guide is adapted to be held in place on the epithelial tissue; inserting the tissue biopsy device within the surgical guide; sampling with the tissue biopsy device; and withdrawing the tissue biopsy device from the surgical guide, where the tissue biopsy device is partially inserted into the surgical guide and then the surgical guide is applied adjacent to or inserted into the cavity to contact the epithelial tissue before the tissue biopsy device is fully inserted into the surgical guide to make contact with the epithelial tissue of the cavity.

Other aspects include a method of obtaining a tissue biopsy comprising the steps of directing a surgical guide adjacent to or inside a body cavity onto an epithelial surface, where the surgical guide is adapted to be held in place on the epithelial tissue; inserting the tissue biopsy device within the surgical guide; sampling with the tissue biopsy device; and withdrawing the tissue biopsy device from the surgical guide, where the tissue biopsy device is partially inserted into the surgical guide and then the surgical guide is applied adjacent to or inserted into the cavity to contact the epithelial tissue before the tissue biopsy device is fully inserted into the surgical guide to make contact with the epithelial tissue of the cavity, where the surgical guide is pressed against the epithelial tissue to cause the tissue encircled by the surgical guide to bulge outwards from the epithelial tissue surface towards the tissue biopsy device.

Other aspects include a method of obtaining a tissue biopsy comprising the steps of directing a surgical guide adjacent to or inside a body cavity onto an epithelial surface, where the surgical guide is adapted to be held in place on the epithelial tissue; inserting the tissue biopsy device within the surgical guide; sampling with the tissue biopsy device; and withdrawing the tissue biopsy device from the surgical guide, where the tissue biopsy device is partially inserted into the surgical guide and then the surgical guide is applied adjacent to or inserted into the cavity to contact the epithelial tissue before the tissue biopsy device is fully inserted into the surgical guide to make contact with the epithelial tissue of the cavity, where the surgical guide is pressed against the epithelial tissue to cause the tissue encircled by the surgical guide to bulge outwards from the epithelial tissue surface towards the tissue biopsy device, where applying force to the surgical guide presents the bulging epithelial tissue towards the tissue biopsy device.

Other aspects include a method of obtaining a tissue biopsy comprising the steps of directing a surgical guide adjacent to or inside a body cavity onto an epithelial surface, where the surgical guide is adapted to be held in place on the epithelial tissue; inserting the tissue biopsy device within the surgical guide; sampling with the tissue biopsy device; and withdrawing the tissue biopsy device from the surgical guide, where the tissue biopsy device is withdrawn into the surgical guide and then the surgical guide acts as a sheath encasing the tissue biopsy device to allow the tissue biopsy device to be withdrawn without making contact with other surfaces.

Some aspects of this invention include a method of obtaining a tissue biopsy comprising the steps of applying a cantilever arm with a distal collar to a sharp edge tissue biopsy device, where the cantilever arm is secured around the shaft of the sharp edge tissue biopsy device, where the cantilever arm is positioned distal to the end of the sharp edge tissue biopsy device of between a lower limit of approximately 1 cm; and an upper limit of approximately 3 cm; depressing the sharp edge tissue biopsy device onto epithelial tissue; and using the cantilever arm to hold the sharp edge tissue biopsy device on a specific area of epithelial tissue.

Some aspects of this invention include a method of obtaining a tissue biopsy comprising the steps of applying a cantilever arm with a distal collar to a sharp edge tissue biopsy device, where the cantilever arm is secured around the shaft of the sharp edge tissue biopsy device, where the cantilever arm is positioned distal to the end of the sharp edge tissue biopsy device of between a lower limit of approximately 1 cm; and an upper limit of approximately 3 cm; depressing the sharp edge tissue biopsy device onto epithelial tissue; and using the cantilever arm to hold the sharp edge tissue biopsy device on a specific area of epithelial tissue, where the sharp edge tissue biopsy device is one or both a conventional punch or cutting forceps.

Some aspects of this invention include a biopsy sampling system comprising a surgical guide; and a tissue biopsy device adapted to pass through the surgical guide.

Other aspects include a biopsy sampling system comprising a surgical guide; and a tissue biopsy device adapted to pass through the surgical guide, further comprising means to visualize the tissue biopsy device inside the tube.

Other aspects include a biopsy sampling system comprising a surgical guide; and a tissue biopsy device adapted to pass through the surgical guide, where the surgical guide is made from plastic, opaque glass, transparent glass, carbon polymer, or metal.

Other aspects include a biopsy sampling system comprising a surgical guide; and a tissue biopsy device adapted to pass through the surgical guide, where the surgical guide is flexible.

Other aspects include a biopsy sampling system comprising a surgical guide; and a tissue biopsy device adapted to pass through the surgical guide, where the surgical guide is rigid.

Other aspects include a biopsy sampling system comprising a surgical guide; and a tissue biopsy device adapted to pass through the surgical guide, where the length of the surgical guide is between a lower limit of approximately 50 millimeters; and an upper limit of approximately 30 centimeters.

Other aspects include a biopsy sampling system comprising a surgical guide; and a tissue biopsy device adapted to pass through the surgical guide, where the inner diameter of the surgical guide is between a lower limit of approximately 2 millimeters; and an upper limit of approximately 20 millimeters.

Other aspects include a biopsy sampling system comprising a surgical guide; and a tissue biopsy device adapted to pass through the surgical guide, where the tissue biopsy device is made from one or more materials selected from the group consisting of plastic, metal and carbon polymer.

Other aspects include a biopsy sampling system comprising a surgical guide; and a tissue biopsy device adapted to pass through the surgical guide, where the tissue biopsy device is flexible.

Other aspects include a biopsy sampling system comprising a surgical guide; and a tissue biopsy device adapted to pass through the surgical guide, where the length of the tissue biopsy device is between a lower limit of approximately 50 millimeters; and an upper limit of approximately 30 centimeters.

Other aspects include a biopsy sampling system comprising a surgical guide; and a tissue biopsy device adapted to pass through the surgical guide, further comprising one or more alignment stops associated with the surgical guide, where the one or more alignment stops are engaged by the tissue biopsy device to allow the tissue biopsy device to remain partially inserted or fully inserted in the surgical guide.

Some aspects of the invention include a retention device for assisting in obtaining a biopsy comprising a surgical guide with one or more alignment stops associated with the surgical guide, where the one or more alignment stops are engaged by a tissue biopsy device.

Some aspects of the invention include a method of retaining a tissue biopsy device on a target tissue lesion comprising the steps of inserting a Frictional Tissue Sampling and Collection (FTSC) device including a handle, a head connected to the handle distal from a frictional surface and a pin guide positioned in the center of the head which projects outwards from the bottom of the head distal from the handle, where the pin guide is adapted to be inserted into a target tissue lesion; applying sufficient force to embed and anchor the pin guide in the target tissue lesion; and rotating the FTSC device such that the head rotates about the pin guide, where the pin guide acts as a fulcrum to steady the FTSC device and prevent migration of the head.

Some aspects of the invention include a method of retaining a tissue biopsy device on a target location on and epithelial surface inside or surrounding a body cavity comprising the steps of receiving a Frictional Tissue Sampling and Collection (FTSC) device, including a shaft with a collar and a head attached to the shaft, where the collar is positioned distal to the head by between a lower limit of approximately 1 cm and an upper limit of approximately 3 cm; securing a cantilever arm to the collar of FTSC device; and rotating the FTSC device, where the cantilever arm acts to steady the FTSC device and prevent migration of the head.

Some aspects of the invention include a method of retaining a Frictional Tissue Sampling and Collection (FTSC) device on an epithelial tissue comprising the steps of directing a surgical guide onto the epithelial tissue, applying pressure to the surgical guide to cause the epithelial tissue to bulge, where the pressure is retained through at least steps (b) through (d), inserting the FTSC device within the surgical guide, collecting tissue with the FTSC device from a sampled area and withdrawing the FTSC device from the biopsy site.

Other aspects include a method of retaining a Frictional Tissue Sampling and Collection (FTSC) device on an epithelial tissue comprising the steps of directing a surgical guide onto the epithelial tissue, applying pressure to the surgical guide to cause the epithelial tissue to bulge, where the pressure is retained through at least steps (b) through (d), inserting the FTSC device within the surgical guide, collecting tissue with the FTSC device from a sampled area and withdrawing the FTSC device from the biopsy site, where applying pressure to the surgical guide results in tamponade of the sampled area.

Other aspects include a method of retaining a Frictional Tissue Sampling and Collection (FTSC) device on an epithelial tissue comprising the steps of directing a surgical guide onto the epithelial tissue, applying pressure to the surgical guide to cause the epithelial tissue to bulge, where the pressure is retained through at least steps (b) through (d), inserting the FTSC device within the surgical guide, collecting tissue with the FTSC device from a sampled area and withdrawing the FTSC device from the biopsy site, further comprising applying the pressure in step (b) through step (e) and retaining the pressure while cauterizing the sampled area.

Some aspects of the invention include a method of retaining a Frictional Tissue Sampling and Collection (FTSC) device on an epithelial tissue comprising the steps of directing a surgical guide with a serrated edge onto the epithelial tissue, applying pressure to the surgical guide to secure the surgical guide to the epithelial tissue, where the pressure is applied at least through steps (b) through (d), inserting the FTSC device within the surgical guide, collecting tissue with the FTSC device from a sampled area and withdrawing the FTSC device from the biopsy site.

Some aspects of the invention include a method of retaining a Frictional Tissue Sampling and Collection (FTSC) device on an epithelial tissue comprising the steps of directing a surgical guide with a serrated edge onto the epithelial tissue, applying pressure to the surgical guide to secure the surgical guide to the epithelial tissue, where the pressure is applied at least through steps (b) through (d), inserting the FTSC device within the surgical guide, collecting tissue with the FTSC device from a sampled area and withdrawing the FTSC device from the biopsy site, where the surgical guide has an acute angle edge.

Some aspects of the invention include a method of retaining a Frictional Tissue Sampling and Collection (FTSC) device on an epithelial tissue comprising the steps of directing a surgical guide with a serrated edge onto the epithelial tissue, applying pressure to the surgical guide to secure the surgical guide to the epithelial tissue, where the pressure is applied at least through steps (b) through (d), inserting the FTSC device within the surgical guide, collecting tissue with the FTSC device from a sampled area and withdrawing the FTSC device from the biopsy site, where the surgical guide has an acute angle edge, where the acute angle is between a lower limit of approximately five degrees and an upper limit of approximately eighty five degrees.

Some aspects of the invention include a method of obtaining a tissue biopsy comprising the steps of directing a surgical guide adjacent to or inside a body cavity onto an epithelial surface, where the surgical guide includes a serrated edge proximal to the epithelial tissue, where the serrated edge holds the surgical guide in place on the epithelial tissue; inserting a FTSC device within the surgical guide; rotating the FTSC device; and withdrawing the FTSC device from the surgical guide.

Some aspects of the invention include a method of obtaining a tissue biopsy comprising the steps of directing a surgical guide adjacent to or inside a body cavity onto an epithelial surface, where the surgical guide is adapted to be held in place on the epithelial tissue; inserting a FTSC device within the surgical guide; depressing the surgical guide to cause the epithelial tissue to bulge outwards; sampling with the tissue biopsy device; releasing the pressure on the surgical guide; and withdrawing the tissue biopsy device from the surgical guide.

Some aspects of the invention include a biopsy sampling and cauterizing system comprising a surgical guide; a tissue biopsy sampling device adapted to pass through the surgical guide; and one or both a cauterizing agent or device, where the one or both a cauterizing agent and device are adapted to pass through the surgical guide.

Some aspects of the invention include a method of retaining a tissue biopsy device on a target location of an epithelial surface comprising the steps of inserting a spiral brush biopsy device including a pin guide positioned in the center of the spiral brush biopsy device and which projects outwards from the bottom of the spiral brush biopsy device into a target tissue lesion; applying sufficient force to anchor the pin guide in the target tissue lesion; and rotating the spiral brush biopsy device such that the spiral brush biopsy device rotates about the pin, where the pin acts as a fulcrum to steady the spiral brush biopsy device and prevent migration of the spiral brush biopsy device.

Some aspects of the invention include a method of obtaining a tissue biopsy comprising the steps of applying a cantilever arm with a distal collar to a biopsy brush device, where the cantilever arm is secured around the shaft of the biopsy brush device, where the cantilever arm is positioned distal to the end of the biopsy brush device of between a lower limit of approximately 1 cm and an upper limit of approximately 3 cm; depressing the biopsy brush device onto epithelial tissue; rotating the biopsy brush device; and using the cantilever arm to hold the biopsy brush device on a specific area of epithelial tissue.

Some aspects of the invention include a method of applying a hemostatic agent to a bleeding biopsy site comprising directing a surgical guide adjacent to the bleeding biopsy site; applying pressure to the surgical guide onto the tissue surrounding the bleeding biopsy site; applying the hemostatic agent through the surgical guide onto the bleeding biopsy site; and releasing the pressure applied to the surgical guide and withdrawing the surgical guide.

Other aspects include a method of applying a hemostatic agent to a bleeding biopsy site comprising directing a surgical guide adjacent to the bleeding biopsy site; applying pressure to the surgical guide onto the tissue surrounding the bleeding biopsy site; applying the hemostatic agent through the surgical guide onto the bleeding biopsy site; and releasing the pressure applied to the surgical guide and withdrawing the surgical guide, where the hemostatic agent is one or both a gel and a solution.

Other aspects include a method of applying a hemostatic agent to a bleeding biopsy site comprising directing a surgical guide adjacent to the bleeding biopsy site; applying pressure to the surgical guide onto the tissue surrounding the bleeding biopsy site; applying the hemostatic agent through the surgical guide onto the bleeding biopsy site; and releasing the pressure applied to the surgical guide and withdrawing the surgical guide, where the hemostatic agent is applied with an applicator passed through the tube and pressed on the bleeding biopsy site directly.

Some aspects of the invention include a surgical guide for holding a tissue surface sampling device 'in place' comprising a tube with a proximal end and a distal end, where the proximal end is beveled to match the tissue surface contour, where the distal end is flat to allow even access to a biopsy device, where the beveled end is serrated to grip the tissue surface.

Other aspects include a surgical guide for holding a tissue surface sampling device 'in place' comprising a tube with a proximal end and a distal end, where the proximal end is beveled to match the tissue surface contour, where the distal end is flat to allow even access to a biopsy device, where the beveled end is serrated to grip the tissue surface, further comprising a camera to one or both direct a FTSC device to the surgical guide and direct the FTSC device onto the tissue surface.

Other aspects include a surgical guide for holding a tissue surface sampling device 'in place' comprising a tube with a proximal end and a distal end, where the proximal end is beveled to match the tissue surface contour, where the distal end is flat to allow even access to a biopsy device, where the beveled end is serrated to grip the tissue surface, further comprising a radio frequency identification (RFID) tag to one or both direct a FTSC device to the surgical guide and direct the FTSC device onto the tissue surface.

Other aspects include a surgical guide for holding a tissue surface sampling device 'in place' comprising a tube with a proximal end and a distal end, where the proximal end is beveled to match the tissue surface contour, where the distal end is flat to allow even access to a biopsy device, where the beveled end is serrated to grip the tissue surface, further comprising a radio opaque material to one or both direct a FTSC device to the surgical guide and direct the FTSC device onto the tissue surface.

Other aspects include a surgical guide for holding a tissue surface sampling device 'in place' comprising a tube with a proximal end and a distal end, where the proximal end is beveled to match the tissue surface contour, where the distal end is flat to allow even access to a biopsy device, where the beveled end is serrated to grip the tissue surface, further comprising a FTSC stop to allow the FTSC device to be partially inserted into the surgical guide and subsequently released from the FTSC stop to allow the FTSC device to contact the tissue surface.

Other aspects include a surgical guide for holding a tissue surface sampling device 'in place' comprising a tube with a proximal end and a distal end, where the proximal end is beveled to match the tissue surface contour, where the distal end is flat to allow even access to a biopsy device, where the beveled end is serrated to grip the tissue surface, further comprising a RFID tag reader to read a RFID tag of a FTSC device.

Other aspects include a surgical guide for holding a tissue surface sampling device 'in place' comprising a tube with a proximal end and a distal end, where the proximal end is beveled to match the tissue surface contour, where the distal end is flat to allow even access to a biopsy device, where the beveled end is serrated to grip the tissue surface, further comprising a RFID tag reader to read a RFID tag of a FTSC device, where the RFID tag reader is adapted to recognize the FTSC device and retrieve previous use data of the FTSC device.

Some aspects of the invention include a method of obtaining a tissue biopsy comprising the steps of directing a surgical guide adjacent to an epithelial surface, where the surgical guide is adapted to be held in place on the epithelial tissue; inserting a sharp edged tissue biopsy device within the surgical guide; depressing the surgical guide to cause the epithelial tissue to bulge outwards; sampling with the sharp-edged tissue biopsy device; releasing the pressure on the surgical guide; and withdrawing the sharp edged tissue biopsy device with the biopsy sample.

Some aspects of the invention include a method of obtaining a tissue biopsy comprising the steps of directing a surgical guide adjacent to an epithelial surface, where the surgical guide is adapted to be held in place on the epithelial tissue; inserting a sharp edged tissue biopsy device within the surgical guide; depressing the surgical guide to cause the epithelial tissue to bulge outwards; sampling with the sharp-edged tissue biopsy device; releasing the pressure on the surgical guide; and withdrawing the sharp edged tissue biopsy device with the biopsy sample, where the sharp edge tissue biopsy device is one or both a conventional punch or cutting forceps.

Some aspects of the invention include a method of applying a medicinal agent to a target site comprising directing a surgical guide adjacent to the target site; applying pressure to the surgical guide onto the tissue surrounding the target site; applying the medicinal agent through the surgical guide onto the target site; and releasing the pressure applied to the surgical guide and withdrawing the surgical guide.

Other aspects include a method of applying a medicinal agent to a target site comprising directing a surgical guide adjacent to the target site; applying pressure to the surgical guide onto the tissue surrounding the target site; applying the medicinal agent through the surgical guide onto the target site; and releasing the pressure applied to the surgical guide and withdrawing the surgical guide, where the medicinal agent is one or both a gel and a solution.

Other aspects include a method of applying a medicinal agent to a target site comprising directing a surgical guide adjacent to the target site; applying pressure to the surgical guide onto the tissue surrounding the target site; applying the medicinal agent through the surgical guide onto the target site; and releasing the pressure applied to the surgical guide and withdrawing the surgical guide, where the medicinal agent is applied with an applicator passed through the tube and pressed on the target site directly.

What is claimed is:

1. A method of obtaining a histology tissue biopsy sample comprising the steps of:
    a) directing a surgical guide adjacent to a first surface on skin, where the surgical guide has a proximal end and a distal end, where at least the proximal end of the surgical guide is adapted to be held in place on the first surface of the skin;
    b) inserting a minimally invasive tissue biopsy device within the surgical guide, where the minimally invasive tissue biopsy device is selected from the group consisting of a cytology brush, a semi-rigid histology sampling brush, a rigid deep epithelial histology sampling brush, a brush that employs bristles, a device that employs a sampling fabric and a trans-epithelial sampling device that employs a sampling fabric material;
    c) applying a first force which contacts the surgical guide, where the first force applies sufficient pressure to the first surface through the proximal end to curtail venous egress to form a bulge of the skin outwards towards the distal end;
    d) frictionally rotating the minimally invasive tissue biopsy device to obtain a histology tissue biopsy sample from the bulge of the skin, where the frictional rotation applies a second force to the first surface;
    e) releasing the pressure on the surgical guide; and
    f) withdrawing the minimally invasive tissue biopsy device with the histology tissue biopsy sample.

2. The method of claim 1, where in one or both step (c) and (d) one or both the first force and the second force is applied by a medical professional.

3. The method of claim 1, where the minimally invasive tissue biopsy device is partially inserted into the surgical guide and then the surgical guide is applied adjacent to the first surface to contact the skin before the minimally invasive tissue biopsy device is fully inserted into the surgical guide to make contact with the first surface.

4. The method of claim 1, where the proximal end of the surgical guide has an acute angle profile end adapted to sample an oblique epithelial surface.

5. The method of claim 1, where the minimally invasive tissue biopsy device is fully inserted into the surgical guide and then the surgical guide is applied adjacent to the first surface to contact the first surface of the skin as the minimally invasive tissue biopsy device makes contact with the first surface.

6. The method of claim 1, where applying the first force to the surgical guide visually changes a surface profile of the first surface presented to the minimally invasive tissue biopsy device.

7. The method of claim 1, where applying the first force to the surgical guide visually changes radius of curvature of the first surface presented to the minimally invasive tissue biopsy device.

8. The method of claim 1, where the skin is non mucosal tissue.

9. The method of claim 1, where the surgical guide is a sheath and the minimally invasive tissue biopsy device is withdrawn into the surgical guide to allow the minimally invasive tissue biopsy device to be withdrawn without making contact with other epithelial surfaces.

10. The method of claim 1, where the proximal end of the surgical guide has an acute angle profile end adapted to sample an oblique epithelial surface and the distal end has a right angle profile allowing pressure to be applied to the surgical guide.

11. The method of claim 1, where the proximal end of the surgical guide has a right angle profile adapted to sample the first surface from directly above and the distal end has an acute angle profile end allowing pressure to be applied to the surgical guide.

12. The method of claim 1, where the proximal end of the surgical guide is serrated to hold the proximal end of the surgical guide in place on the skin to restrict the minimally invasive tissue biopsy device within the surgical guide to obtain the histology tissue biopsy sample.

13. The method of claim 1, where the minimally invasive tissue biopsy device includes a sampling surface, where the sampling surface is oriented perpendicular to the main axis of the surgical guide.

14. A method of obtaining a tissue biopsy sample of a lesion on an oblique skin first surface comprising the steps of:
    a) selecting as a proximal end of a surgical guide from the group consisting of a right angle profile end adapted to sample an oblique epithelial skin first surface and an acute angle profile end adapted to sample the oblique epithelial skin first surface;
    b) directing the proximal end of the surgical guide visually adjacent to the oblique epithelial skin first surface of a suspected neoplastic lesion to circumferentially surround the oblique epithelial skin first surface of the suspected neoplastic lesion, where the surgical guide is visually directed to circumferentially surround an area of the suspected neoplastic lesion on the oblique epithelial skin first surface;
    c) applying a first force which contacts the surgical guide, where the first force applies pressure to the oblique epithelial skin first surface surrounding the suspected neoplastic lesion through the proximal end to cause the oblique epithelial skin first surface to form a bulge outwards away from the proximal end, where the surgical guide prevents migration of a minimally invasive tissue biopsy device away from the suspected neoplastic lesion during sampling;
    d) inserting the minimally invasive tissue biopsy device with an abrasive surface oriented parallel to the plane of the oblique epithelial skin first surface within the surgical guide, where the minimally invasive tissue biopsy device is selected from the group consisting of a cytology brush, a semi-rigid histology sampling brush, a rigid deep epithelial histology sampling brush, a brush that employs bristles, a device that employs a sampling fabric and a trans-epithelial sampling device that employs a sampling fabric material;
    e) applying a second force to the minimally invasive tissue biopsy device to obtain a histology tissue biopsy sample of the suspected neoplastic lesion on the bulge on the oblique epithelial skin first surface;
    f) releasing the second force; and
    g) withdrawing the minimally invasive tissue biopsy device with the histology tissue biopsy sample.

15. The method of claim 14, where the minimally invasive tissue biopsy device is partially inserted into the surgical guide and then the surgical guide is applied adjacent to contact the oblique epithelial skin first surface before the minimally invasive tissue biopsy device is fully inserted into the surgical guide to make contact with the oblique epithelial tissue first surface.

16. The method of claim 14, where the minimally invasive tissue biopsy device includes a sampling surface, where the sampling surface is oriented parallel with the first surface.

17. A method of obtaining a tissue biopsy sample comprising the steps of:
   a) directing a surgical guide including a wall adjacent to a first surface on skin, where the surgical guide is visually directed perpendicular relative to the first surface to circumferentially surround an area of the first surface;
   b) applying a contact force which contacts the surgical guide, where the contact force applies sufficient pressure to the first surface to form a firm turgid base on the first surface surrounded by the wall;
   c) inserting a minimally invasive tissue biopsy device within the surgical guide, where the minimally invasive tissue biopsy device is inserted within the surgical guide by the medical professional, where the minimally invasive tissue biopsy device is selected from the group consisting of a cytology brush, a semi-rigid histology sampling brush, a rigid deep epithelial histology sampling brush, a brush that employs bristles, a device that employs a sampling fabric and a trans-epithelial sampling device that employs a sampling fabric material;
   d) applying a frictional force to the minimally invasive tissue biopsy device to the firm turgid base;
   e) sampling with the minimally invasive tissue biopsy device the firm turgid base on the first surface surrounded by the wall of the surgical guide to achieve frictional abrasion to obtain a histology tissue biopsy sample of the first surface on the skin;
   f) releasing the frictional force from the minimally invasive tissue biopsy device; and
   g) withdrawing the minimally invasive tissue biopsy device with the histology tissue biopsy sample.

18. The method of claim 17, further comprising withdrawing the minimally invasive tissue biopsy device within the surgical guide.

19. The method of claim 17, where sampling with the minimally invasive tissue biopsy device includes rotating the minimally invasive tissue biopsy device within the surgical guide to apply the frictional force to the first surface to obtain the tissue biopsy sample.

20. The method of claim 17, where the minimally invasive tissue biopsy device includes a sampling surface, where the sampling surface is oriented adjacent to the first surface.

* * * * *